(12) United States Patent
Pitterna et al.

(10) Patent No.: US 10,155,730 B2
(45) Date of Patent: Dec. 18, 2018

(54) ISOXAZOLINE DERIVATIVES AS INSECTICIDES

(71) Applicant: Syngenta Crop Protection LLC, Greensboro, NC (US)

(72) Inventors: Thomas Pitterna, Stein (CH); Myriem El Qacemi, Stein (CH); Jerome Yves Cassayre, Stein (CH); Peter Renold, Stein (CH); Vladimir Bobosik, Bratislava (SK)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 15/252,782

(22) Filed: Aug. 31, 2016

(65) Prior Publication Data

US 2016/0368883 A1 Dec. 22, 2016

Related U.S. Application Data

(62) Division of application No. 14/275,989, filed on May 13, 2014, now Pat. No. 9,456,605, which is a division of application No. 13/579,637, filed as application No. PCT/EP2011/052336 on Feb. 17, 2011, now Pat. No. 8,754,053.

(30) Foreign Application Priority Data

Feb. 17, 2010 (EP) .................... 10153831

(51) Int. Cl.
| | | |
|---|---|---|
| C07D 261/04 | (2006.01) | |
| C07D 413/10 | (2006.01) | |
| A01N 43/80 | (2006.01) | |
| C07D 413/12 | (2006.01) | |
| C07D 417/12 | (2006.01) | |

(52) U.S. Cl.
CPC ........... C07D 261/04 (2013.01); A01N 43/80 (2013.01); C07D 413/10 (2013.01); C07D 413/12 (2013.01); C07D 417/12 (2013.01)

(58) Field of Classification Search
None
See application file for complete search history.

(56) References Cited

FOREIGN PATENT DOCUMENTS

| EP | 1731512 A1 | 12/2006 |
|---|---|---|
| EP | 2151437 A1 | 2/2010 |
| EP | 2172448 | 4/2010 |
| EP | 2199287 | 6/2010 |
| JP | 2009108046 A | 5/2009 |
| WO | 2008019760 | 2/2008 |
| WO | 2008122375 A2 | 10/2008 |
| WO | 2009005015 A1 | 1/2009 |
| WO | 2009035004 A1 | 3/2009 |

OTHER PUBLICATIONS

International Search Report and Written Opinion dated Apr. 18, 2011 for International Patent Application No. PCT/EP2011/052336.
International Preliminary Report on Patentability dated Aug. 21, 2012 for International Patent Application No. PCT/EP2011/052336.

*Primary Examiner* — Kamal A Saeed
(74) *Attorney, Agent, or Firm* — Dinsmore & Shohl LLP; Toni-Junell Herbert

(57) ABSTRACT

The present invention relates to compounds formula (I):

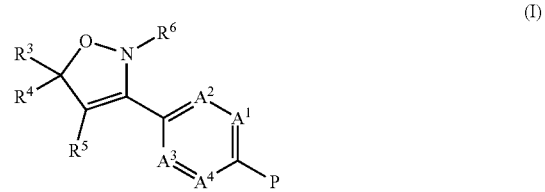

(I)

wherein
P is P1, P2, heterocyclyl or heterocyclyl substituted by one to five Z;

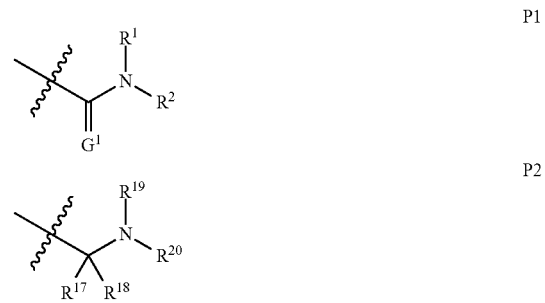

and wherein $A^1$, $A^2$, $A^3$, $A^4$, $G^1$, $R^1$, $R^2$, $R^3$, $R^4$, $R^5$, $R^6$, $R^{17}$, $R^{18}$, $R^{19}$ and $R^{20}$ are as defined herein; or a salt or N-oxide thereof.

Furthermore, the present invention relates to processes and intermediates for preparing compounds of formula (I), to insecticidal, acaricidal, nematicidal and molluscicidal compositions comprising the compounds of formula (I) and to methods of using the compounds of formula (I) to control insect, acarine, nematode and mollusc pests.

1 Claim, No Drawings

ISOXAZOLINE DERIVATIVES AS INSECTICIDES

RELATED APPLICATION INFORMATION

This application is a divisional of U.S. patent application Ser. No. 14/275,989 filed May 13, 2014, which is a divisional of U.S. patent application Ser. No. 13/579,637 which was filed on Aug. 17, 2012, and was issued as U.S. Pat. No. 8,754,053 granted on Jun. 17, 2014, which is a 371 of International Application No. PCT/EP2011/052336, filed Feb. 17, 2011, which claims priority to EP Patent Application No. 10153831.2, filed Feb. 17, 2010, the contents of which are incorporated herein by reference herein.

The present invention relates to certain 2,5-dihydro-isoxazoline derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain 4,5-dihydro-isoxazoline derivatives with insecticidal properties are disclosed, for example, in EP 1,731,512.

It has now surprisingly been found that certain 2,5-dihydro-isoxazoline derivatives have insecticidal properties.

The present invention therefore provides a compound of formula (I)

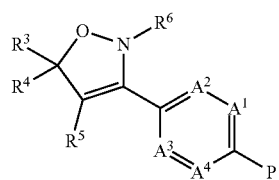

(I)

wherein
P is P1, P2, heterocyclyl or heterocyclyl substituted by one to five Z;

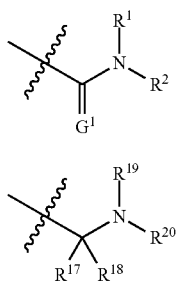

P1

P2

$A^1$, $A^2$, $A^3$ and $A^4$ are independently of each other C—H, C—$R^7$, or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$ aryl or aryl substituted by one to five $R^{10}$, heterocyclyl or heterocyclyl substituted by one to five $R^{10}$, $C_1$-$C_8$alkylaminocarbonyl-$C_1$-$C_4$alkylene, $C_1$-$C_8$haloalkylaminocarbonyl-$C_1$-$C_4$alkylene, $C_3$-$C_8$cycloalkyl-aminocarbonyl-$C_1$-$C_4$alkylene, $C_1$-$C_6$alkyl-O—N=CH—, or $C_1$-$C_6$haloalkyl-O—N=CH—;
$R^3$ is $C_1$-$C_8$haloalkyl;
$R^4$ is aryl or aryl substituted by one to five $R^{11}$, or heteroaryl or heteroaryl substituted by one to five $R^{11}$;
$R^5$ is hydrogen;
$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$ aryl or aryl substituted by one to five $R^{14}$, heterocyclyl or heterocyclyl substituted by one to five $R^{14}$, $C_1$-$C_4$alkoxycarbonyl-, $C_1$-$C_4$alkenyloxycarbonyl-, $C_1$-$C_4$alkynyloxycarbonyl-, or benzyloxycarbonyl- or benzyloxycarbonyl- in which the benzyl group is optionally substituted by one to five $R^{16}$;
each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^8$ is independently halogen, cyano, nitro, hydroxy, amino, $C_1$-$C_8$alkylamino, ($C_1$-$C_8$alkyl)$_2$amino, $C_1$-$C_8$alkylcarbonylamino, $C_1$-$C_8$haloalkylcarbonylamino, $C_1$-$C_8$alkoxy-, $C_1$-$C_8$haloalkoxy-, aryloxy or aryloxy substituted by one to five $R^{15}$, aryloxy-$C_1$-$C_4$alkylene or aryloxy-$C_1$-$C_4$alkylene wherein the aryl moiety is substituted by one to five $R^{15}$, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, or aryl-$C_1$-$C_4$alkylthio- or aryl-$C_1$-$C_4$alkylthio- wherein the aryl moiety is substituted by one to five $R^{15}$;
each $R^9$ is independently halogen, $C_1$-$C_8$alkyl, $C_1$-$C_8$alkenyl, $C_1$-$C_8$alkynyl, $C_1$-$C_8$alkyl-O—N=, $C_1$-$C_8$haloalkyl-O—N=, $C_1$-$C_8$alkoxy or $C_1$-$C_8$alkoxycarbonyl;
each $R^{10}$ is independently halogen, cyano, nitro, oxo, $C_1$-$C_8$alkyl, $C_1$-$C_8$haloalkyl, $C_1$-$C_8$cyanoalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkylene, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylaminosulfonyl, ($C_1$-$C_8$alkyl)$_2$aminosulfonyl-, $C_1$-$C_8$alkylcarbonyl-, $C_1$-$C_8$alkoxycarbonyl-, aryl or aryl substituted by one to five $R^{15}$, heterocyclyl or heterocyclyl substituted by one to five $R^{15}$, aryl-$C_1$-$C_4$alkylene or aryl-$C_1$-$C_4$alkylene wherein the aryl moiety is substituted by one to five $R^{15}$, heterocyclyl-$C_1$-$C_4$alkylene or heterocyclyl-$C_1$-$C_4$alkylene wherein the heterocyclyl moiety is substituted by one to five $R^{15}$, aryloxy or aryloxy substituted by one to five $R^{15}$, aryloxy-$C_1$-$C_4$alkylene or aryloxy-$C_1$-$C_4$alkylene wherein the aryl moiety is substituted by one to five $R^{15}$; each $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;

each $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^{13}$ is independently halogen or $C_1$-$C_8$alkyl;

each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;

each $R^{16}$ is independently halogen, cyano, formyl, $C_1$-$C_4$alkyl, $C_1$-$C_4$haloalkyl, $C_1$-$C_4$alkoxy, $C_1$-$C_4$haloalkoxy, $C_3$-$C_6$cycloalkyl;

$R^{17}$ and $R^{18}$ are independently halogen, hydrogen, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, cyano, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, or $R^{17}$ and $R^{18}$ together with the carbon atom to which they are attached may form a 3 to 6-membered carbocyclic ring;

$R^{19}$ is hydrogen, $NH_2$, hydroxyl, $C_1$-$C_{12}$alkoxy or $C_1$-$C_{12}$alkoxy substituted by one to five $R^8$, $C_1$-$C_{12}$alkylcarbonylamino or $C_1$-$C_{12}$alkylcarbonylamino wherein the alkyl is substituted by one to five $R^8$, $C_1$-$C_{12}$alkylamino or $C_1$-$C_{12}$alkylamino wherein the alkyl is substituted by one to five $R^8$, $C_1$-$C_{12}$alkyl or $C_1$-$C_{12}$alkyl substituted by one to five $R^8$, $C_3$-$C_8$cycloalkyl or $C_3$-$C_8$cycloalkyl substituted by one to five $R^9$, cyano, $C_2$-$C_{12}$alkenyl or $C_2$-$C_{12}$alkenyl substituted by one to five $R^8$, $C_2$-$C_{12}$alkynyl or $C_2$-$C_{12}$alkynyl substituted by one to five $R^8$, $C_1$-$C_{12}$alkylcarbonyl or $C_1$-$C_{12}$alkylcarbonyl substituted by one to five $R^8$, $C_1$-$C_{12}$alkoxycarbonyl or $C_1$-$C_{12}$alkoxycarbonyl substituted by one to five $R^8$, or is selected from $CH_2$—$R^{21}$, $C(=O)R^{21}$ and $C(=S)R^{21}$;

$R^{20}$ is hydrogen, cyano, carbonyl, thiocarbonyl, $C_1$-$C_{12}$alkylcarbonyl or $C_1$-$C_{12}$alkylcarbonyl substituted by one to five $R^8$, $C_1$-$C_{12}$alkylthiocarbonyl or $C_1$-$C_{12}$alkylthiocarbonyl substituted by one to five $R^8$, $C_1$-$C_{12}$alkylaminocarbonyl or $C_1$-$C_{12}$alkylaminocarbonyl wherein the alkyl is substituted by one to five $R^8$, $C_1$-$C_{12}$alkylaminothiocarbonyl or $C_1$-$C_{12}$alkylamino- thiocarbonyl wherein the alkyl is substituted by one to five $R^8$, $C_2$-$C_{24}$ (total carbon number) dialkylaminocarbonyl or $C_2$-$C_{24}$ (total carbon number) dialkylaminocarbonyl wherein one or both alkyl is substituted by one to five $R^8$, $C_2$-$C_{24}$ (total carbon number) dialkylaminothiocarbonyl or $C_2$-$C_{24}$ (total carbon number) dialkylaminothiocarbonyl wherein one or both alkyl is substituted by one to five $R^8$, $C_1$-$C_{12}$alkoxyaminocarbonyl or $C_1$-$C_{12}$alkoxyaminocarbonyl wherein the alkoxy is substituted by one to five $R^8$, $C_1$-$C_{12}$alkoxyaminothiocarbonyl or $C_1$-$C_{12}$alkoxyaminothiocarbonyl wherein the alkoxy is substituted by one to five $R^8$, $C_1$-$C_{12}$alkoxycarbonyl or $C_1$-$C_{12}$alkoxycarbonyl substituted by one to five $R^8$, $C_1$-$C_{12}$alkoxythiocarbonyl or $C_1$-$C_{12}$alkoxythiocarbonyl substituted by one to five $R^8$, $C_1$-$C_{12}$thioalkoxycarbonyl or $C_1$-$C_{12}$thioalkoxycarbonyl substituted by one to five $R^8$, $C_1$-$C_{12}$thioalkoxythiocarbonyl or $C_1$-$C_{12}$thioalkoxythiocarbonyl substituted by one to five $R^8$, $C_1$-$C_{12}$alkylsulfonyl or $C_1$-$C_{12}$alkylsulfonyl substituted by one to five $R^8$, $C_3$-$C_{12}$cycloalkylcarbonyl or $C_3$-$C_{12}$cycloalkylcarbonyl substituted by one to five $R^9$, $C_2$-$C_{12}$alkenylcarbonyl or $C_2$-$C_{12}$alkenylcarbonyl substituted by one to five $R^8$, $C_2$-$C_{12}$alkynylcarbonyl or $C_2$-$C_{12}$alkynylcarbonyl substituted by one to five $R^8$, $C_3$-$C_{12}$cycloalkyl-$C_1$-$C_{12}$alkylcarbonyl or $C_3$-$C_{12}$cycloalkyl-$C_1$-$C_{12}$alkylcarbonyl substituted by one to five $R^9$, $C_1$-$C_{12}$alkylsulfenyl-$C_1$-$C_{12}$alkylcarbonyl or $C_1$-$C_{12}$alkylsulfenyl-$C_1$-$C_{12}$alkylcarbonyl substituted by one to five $R^8$, $C_1$-$C_{12}$ alkylsulfinyl-$C_1$-$C_{12}$alkylcarbonyl or $C_1$-$C_{12}$ alkylsulfinyl-$C_1$-$C_{12}$alkylcarbonyl substituted by one to five $R^8$, $C_1$-$C_{12}$ alkylsulfonyl-$C_1$-$C_{12}$alkylcarbonyl or $C_1$-$C_{12}$alkylsulfonyl-$C_1$-$C_{12}$alkylcarbonyl substituted by one to five $R^8$, $C_1$-$C_{12}$alkylcarbonyl-$C_1$-$C_{12}$alkylcarbonyl or $C_1$-$C_{12}$alkylcarbonyl-$C_1$-$C_{12}$alkylcarbonyl substituted by one to five $R^8$, $C_3$-$C_{12}$ cycloalkylaminocarbonyl or $C_3$-$C_{12}$cycloalkylaminocarbonyl wherein the cycloalkyl is substituted by one to five $R^9$, $C_2$-$C_{12}$alkenylaminocarbonyl or $C_2$-$C_{12}$alkenylaminocarbonyl wherein the alkenyl is substituted by one to five $R^8$, $C_2$-$C_{12}$alkynylaminocarbonyl or $C_2$-$C_{12}$alkynylaminocarbonyl wherein the alkynyl is substituted by one to five $R^8$, or is selected from $C(=O)R^{21}$ and $C(=S)R^{21}$; or $R^{19}$ and $R^{20}$ together with the nitrogen atom to which they are bound, form a 3- to 6-membered heterocyclic ring which may be substituted by one to five $R^{22}$, or may be substituted with a keto, thioketo or nitroimino group;

$R^{21}$ is aryl or aryl substituted by one to five $R^{22}$, heterocyclyl or heterocyclyl substituted by one to five $R^{22}$, aryl-$C_1$-$C_4$alkylene or aryl-$C_1$-$C_4$alkylene wherein the aryl moiety is substituted by one to five $R^{22}$, or heterocyclyl-$C_1$-$C_4$alkylene or heterocyclyl-$C_1$-$C_4$alkylene wherein the heterocyclyl moiety is substituted by one to five $R^{22}$;

each $R^{22}$ is independently halogen, cyano, nitro, oxo, $C_1$-$C_8$alkyl, $C_1$-$C_8$haloalkyl, $C_1$-$C_8$alkoxy, $C_1$-$C_8$haloalkoxy, $C_1$-$C_8$alkoxycarbonyl, $C_1$-$C_8$alkyl-N=, $C_1$-$C_8$haloalkyl-N=, $C_1$-$C_8$alkylthio, $C_1$-$C_8$haloalkylthio, or phenyl or phenyl substituted by one to five halogen; each Z is independently halogen, $C_1$-$C_{12}$alkyl or $C_1$-$C_{12}$alkyl substituted by one to five $R^8$, nitro, $C_1$-$C_{12}$alkoxy or $C_1$-$C_{12}$alkoxy substituted by one to five $R^8$, cyano, $C_1$-$C_{12}$alkylsulfinyl, $C_1$-$C_{12}$alkylsulfonyl, $C_1$-$C_{12}$haloalkylsulfinyl, $C_1$-$C_{12}$haloalkylsulfonyl, hydroxyl or thiol; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, at the —$CR^3R^4$— group, and may exist as enantiomers (or as pairs of diastereo-isomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of P, $A^1$, $A^2$, $A^3$, $A^4$, $G^1$, $R^1$, $R^2$, $R^3$, $R^4$, $R^6$, $R^7$, $R^8$, $R^9$, $R^{10}$, $R^{11}$, $R^{12}$, $R^{13}$, $R^{14}$, $R^{15}$, $R^{16}$ $R^{17}$, $R^{18}$, $R^{19}$, $R^{20}$, $R^{21}$ and $R^{22}$ are, in any combination, as set out below.

Preferably, P is P1, P2, or a heterocycle selected from H1 to H9

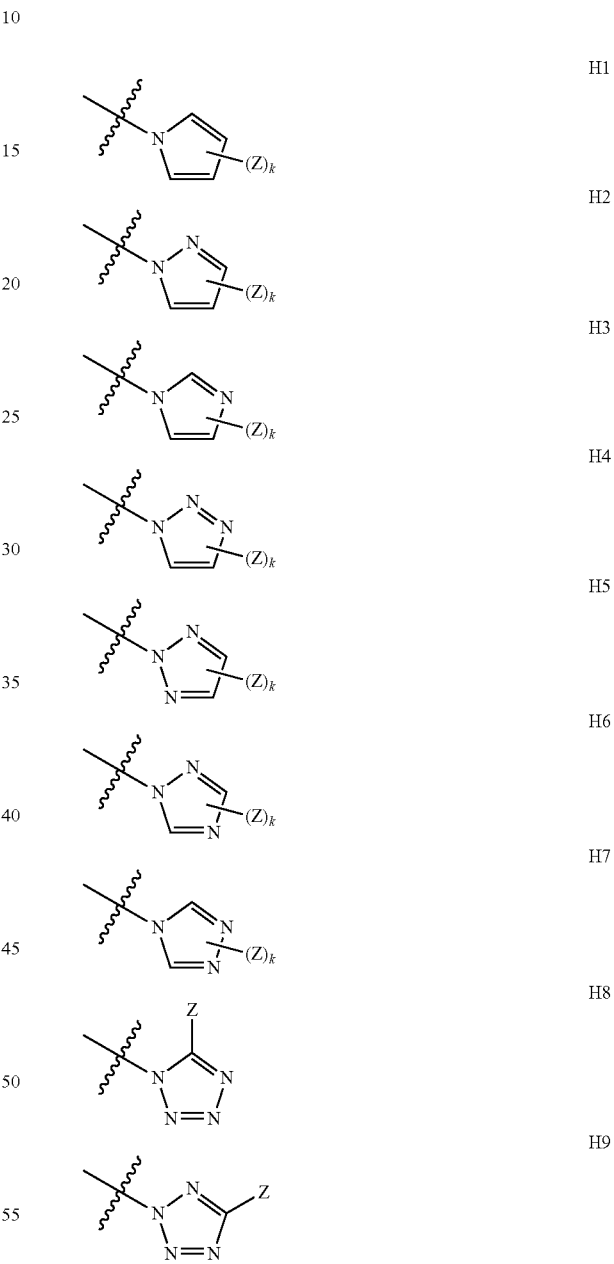

k is 0, 1 or 2.

In one group of compounds P is P1. In another group of compounds P is P2. In another group of compounds P is a heterocycle selected from H1-H9.

Preferably no more than two of $A^1$, $A^2$, $A^3$ and $A^4$ are nitrogen, more preferably no more than one of $A^1$, $A^2$, $A^3$ and $A^4$ is nitrogen.

Preferably no more than two of $A^1$, $A^2$, $A^3$ and $A^4$ are nitrogen.

Preferably $A^1$ is C—H or C—$R^7$, most preferably $A^1$ is C—$R^7$.

Preferably $A^2$ is C—H or C—$R^7$, most preferably $A^2$ is C—H.

Preferably $A^3$ is C—H or C—$R^7$, most preferably $A^3$ is C—H.

Preferably $A^4$ is C—H or C—$R^7$, most preferably $A^4$ is C—H.

In one preferred group of compounds $A^1$ is C—$R^7$, $A^2$ is C—H, $A^3$ is C—H or nitrogen and $A^4$ is C—H or nitrogen.

In another preferred group of compounds $A^1$ is C—$R^7$, $A^2$ is C—H, $A^3$ is C—H and $A^4$ is C—H.

Preferably $G^1$ is oxygen.

Preferably $R^1$ is hydrogen, methyl, ethyl, methylcarbonyl-, or methoxycarbonyl-, more preferably hydrogen, methyl or ethyl, most preferably hydrogen.

Preferably, $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, $C_3$-$C_8$cycloalkyl-aminocarbonyl-$C_1$-$C_4$ alkylene, or group A

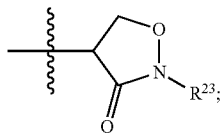

(A)

wherein $R^{23}$ is hydrogen, methyl, ethyl, propyl, isopropyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, benzyl, benzyl substituted by one to three $R^{12}$, or $R^{11}$ is pyridyl-methyl- or pyridyl-methyl-substituted by one to three $R^{12}$; and each $R^{12}$ is independently fluoro, chloro, bromo, trifluoromethyl, trifluoromethoxy, cyano or methoxy. Preferably each aryl group is a phenyl group and each heterocycle group is selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]-dioxinyl.

Preferably $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]dioxinyl.

More preferably $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, tetrahydrofuranyl-$C_1$-$C_4$alkylene- or tetrahydrofuranyl-$C_1$-$C_4$alkylene- wherein the tetrahydrofuranyl moiety is substituted by one to five $R^{10}$, imidazolyl-$C_1$-$C_4$alkylene- or imidazolyl-$C_1$-$C_4$alkylene- wherein the imidazolyl moiety is substituted by one to three $R^{10}$ pyrazolyl-$C_1$-$C_4$alkylene- or pyryazolyl-$C_1$-$C_4$alkylene- wherein the pyrazolyl moiety is substituted by one to three $R^{10}$, pyrrolyl-$C_1$-$C_4$alkylene- or pyrrolyl-$C_1$-$C_4$alkylene- wherein the pyrrolyl moiety is substituted by one to four $R^{10}$, thiazolyl-$C_1$-$C_4$alkylene- or thiazolyl-$C_1$-$C_4$alkylene- wherein the thiazolyl moiety is substituted by one to four $R^{10}$, oxetanyl or oxetanyl substituted by one to five $R^{10}$, thietanyl or thietanyl substituted by one to five $R^{10}$ oxo-thietanyl or oxo-thietanyl substituted by one to five $R^{10}$, dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, for example $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, tetrahydrofuranyl-$C_1$-$C_4$alkylene- or tetrahydrofuranyl-$C_1$-$C_4$alkylene- wherein the tetrahydrofuranyl moiety is substituted by one to five $R^{10}$, imidazolyl-$C_1$-$C_4$alkylene- or imidazolyl-$C_1$-$C_4$alkylene- wherein the imidazolyl moiety is substituted by one to three $R^{10}$ pyrazolyl-$C_1$-$C_4$alkylene- or pyryazolyl-$C_1$-$C_4$alkylene- wherein the pyrazolyl moiety is substituted by one to three $R^{10}$, pyrrolyl-$C_1$-$C_4$alkylene- or pyrrolyl-$C_1$-$C_4$alkylene- wherein the pyrrolyl moiety is substituted by one to four $R^{10}$, thiazolyl-$C_1$-$C_4$alkylene- or thiazolyl-$C_1$-$C_4$alkylene- wherein the thiazolyl moiety is substituted by one to four $R^{10}$, oxetanyl or oxetanyl substituted by one to five $R^{10}$, thietanyl or thietanyl substituted by one to five $R^{10}$ oxo-thietanyl or oxo-thietanyl substituted by one to five $R^{10}$, or dioxo-thietanyl or dioxo-thietanyl substituted by one to five $R^{10}$.

Even more preferably $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, for example $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, or dioxo-thietanyl or dioxo-thietanyl substituted by one to five $R^{10}$, more preferably $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl, dioxo-thietanyl, $C_1$-$C_8$alkylaminocarbonyl-methylene, $C_1$-$C_8$haloalkylaminocarbonyl-methylene, or $C_3$-$C_8$cycloalkyl-aminocarbonyl-methylene, for example $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to four $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl or dioxo-thietanyl, most preferably butyl-, cyclobutyl-, 1-phenyl-eth-1-yl-, phenyl-methyl-, (pyrid-2-yl)-methyl-, thietanyl-, oxo-thietanyl- or dioxo-thietanyl-.

A group of preferred compounds are those wherein $R^2$ is $C_1$-$C_6$alkyl or $C_1$-$C_6$alkyl substituted by one to five $R^8$, for example ethyl-, butyl-, but-2-yl-, 3-bromo-propyl-, 2,2,2-trifluoro-ethyl-, 3,3,3-trifluoro-propyl-, 2-methoxy-ethyl-, and 1-methoxy-prop-2-yl-.

A group of preferred compounds are those wherein $R^2$ is $C_3$-$C_8$cycloalkyl or $C_3$-$C_8$cycloalkyl substituted by one to five $R^9$, for example cyclobutyl-, and 2-methyl-cyclohex-1-yl-.

A group of preferred compounds are those wherein $R^2$ is aryl-$C_1$-$C_2$alkylene- or aryl-$C_1$-$C_2$alkylene- wherein the aryl moiety is substituted by one to five $R^{10}$, for example phenyl-methyl-, 1-phenyl-eth-1-yl-, 2-phenyl-eth-1-yl-, (3-chloro-phenyl)-methyl-, (2-fluoro-phenyl)-methyl-, (4-methoxy-phenyl)-methyl-, (2-trifluoromethyl-phenyl)-methyl-, and (2-trifluoromethoxy-phenyl)-methyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^{10}$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl. A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^{10}$, for example (pyrid-2-yl)-methyl-, (pyrid-3-yl)-methyl-, (2-chloro-pyrid-5-yl)-methyl-, (1-methyl-1H-imidazol-4-yl)-methyl-, (furan-2-yl)-methyl-, 2-(thiophen-2'-yl)-eth-1-yl-, 2-(indol-3'-yl)-eth-1-yl-, (1H-benzimidazol-2-yl)-methyl-, (oxetan-2-yl)-methyl-, (tetrahydrofuran-2-yl)-methyl-, 2-([1',3']dioxolan-2'-yl)-eth-1-yl-, 2-(morpholin-4'-yl)-eth-1-yl-, 2-(benzo[1',3']dioxol-5'-yl)-eth-1-yl-, and (2,3-dihydro-benzo[1,4]dioxin-6-yl)-methyl-, more preferably $R^2$ is heteroaryl-$C_1$-$C_2$alkylene- or heteroaryl-$C_1$-$C_2$alkylene- wherein the heteroaryl moiety is substituted by one to five $R^{10}$. A group of preferred compounds are those wherein $R^2$ is aryl or aryl substituted by one to five $R^{10}$, for example 2-chloro-phenyl-, 3-fluoro-phenyl-, 2-methyl-phenyl-, 2-chloro-6-methyl-phenyl-, 2-trifluoromethyl-phenyl-, and 2,4-dimethoxy-phenyl-.

A group of preferred compounds are those wherein $R^2$ is heterocyclyl- or heterocyclyl substituted by one to five $R^{10}$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

A group of preferred compounds are those wherein $R^2$ is heterocyclyl or heterocyclyl substituted by one to five $R^{10}$, for example 3-methyl-pyrid-2-yl-, 1,3-dimethyl-1H-pyrazol-5-yl-, 4-methyl-thiazol-2-yl-, 5-methyl-thiadiazol-2-yl-, quinolin-2-yl-, quinolin-5-yl-, benzothiazol-6-yl-, 4-methyl-benzothiazol-2-yl-, thietan-3-yl-, 1-oxo-thietan-3-yl-, 1,1-dioxo-thietan-3-yl-, and 3-methyl-thietan-3-yl-, more preferably $R^2$ is oxetanyl, thietanyl, oxo-thietanyl or dioxo-thietanyl each optionally substituted by one to five $R^{10}$, most preferably $R^2$ is thietanyl, oxo-thietanyl or dioxo-thietanyl each optionally substituted by one to five $R^{10}$. It is particularly preferred that the oxetanyl, thietanyl, oxo-thietanyl or dioxo-thietanyl ring is linked via the 3-position.

A group of preferred compounds are those wherein $R^2$ is group (A).

Preferably $R^3$ is chlorodifluoromethyl or trifluoromethyl, most preferably trifluoromethyl.

Preferably $R^4$ is aryl or aryl substituted by one to five $R^{11}$, more preferably aryl substituted by one to three $R^{11}$, more preferably phenyl substituted by one to three $R^{11}$, even more preferably 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-, most preferably $R^4$ is 3,5-dichloro-phenyl.

A group of preferred compounds are those wherein $R^6$ is $C_1$-$C_8$alkyl or $C_1$-$C_8$alkyl substituted by one to five $R^{12}$, aryl-$C_1$-$C_4$alkylene- or aryl-$C_1$-$C_4$alkylene- wherein the aryl moiety is substituted by one to five $R^{14}$, heteroaryl-$C_1$-$C_4$alkylene- or heteroaryl-$C_1$-$C_4$alkylene- wherein the heteroaryl moiety is substituted by one to five $R^{14}$, more preferably $C_1$-$C_8$alkyl or $C_1$-$C_8$alkyl substituted by one to five $R^{12}$, phenyl-$C_1$-$C_4$alkylene- or phenyl-$C_1$-$C_4$alkylene- wherein the phenyl moiety is substituted by one to five $R^{14}$, more preferably $C_1$-$C_8$alkyl or $C_1$-$C_8$alkyl substituted by one to five $R^{12}$, phenyl-methylene- or phenyl-methylene wherein the phenyl moiety is substituted by one to five $R^{14}$, more preferably $C_1$-$C_8$alkyl or phenyl-methylene, more preferably $C_1$-$C_8$alkyl, more preferably methyl.

A group of preferred compounds are those where $R^6$ is $C_1$-$C_4$ alkoxycarbonyl-, $C_1$-$C_4$ alkenyloxycarbonyl-, $C_1$-$C_4$ alkynyloxycarbonyl-, benzyloxycarbonyl- or benzyloxycarbonyl- in which the benzyl group is optionally substituted by one to five $R^{16}$, more preferably $R^6$ is methyloxycarbonyl, ethyloxycarbonyl, propyloxycarbonyl, allyloxycarbonyl, propargyloxycarbonyl, benzyloxcarbonyl or benzyloxycarbonyl optionally substituted by one to five $R^{16}$.

Preferably each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkoxy-, or $C_1$-$C_8$haloalkoxy-, more preferably bromo, chloro, fluoro, cyano, nitro, methyl, ethyl, trifluoromethyl, vinyl, methoxy, difluoromethoxy, or trifluoromethoxy, most preferably methyl.

Preferably each $R^8$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, more preferably $C_1$-$C_8$haloalkylsulfonyl-, halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^9$ is independently halogen or $C_1$-$C_8$alkyl, more preferably chloro, fluoro or methyl, most preferably methyl.

Preferably each $R^{10}$ is independently halogen, cyano, nitro, $C_1$-$C_8$alkyl, $C_1$-$C_8$haloalkyl, $C_1$-$C_8$alkoxy-, $C_1$-$C_8$haloalkoxy-, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Preferably each $R^{11}$ is independently halogen, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-, more preferably bromo, chloro, fluoro, trifluoromethyl, methoxy, or methylthio, most preferably bromo or chloro.

Preferably each $R^{12}$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^{13}$ is independently chloro, fluoro or methyl, most preferably methyl.

Preferably each $R^{14}$ is independently halogen, cyano, nitro, $C_1$-$C_8$alkyl, $C_1$-$C_8$haloalkyl, $C_1$-$C_8$alkoxy-, $C_1$-$C_8$haloalkoxy-, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Preferably each $R^{15}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

Preferably each $R^{16}$ is independently $C_1$-$C_4$ alkyl, $C_1$-$C_4$ haloalkyl or halogen, more preferably methyl, ethyl, halomethyl, haloethyl, fluoro, chloro or bromo.

Preferably, $R^{17}$ and $R^{18}$ are each independently hydrogen, halogen, $C_1$-$C_{12}$alkyl, $C_1$-$C_{12}$haloalkyl, $C_3$-$C_8$cycloalkyl, $C_3$-$C_8$halocycloalkyl, $C_2$-$C_{12}$alkenyl or $C_2$-$C_{12}$haloalkenyl, $C_2$-$C_{12}$alkynyl, $C_2$-$C_{12}$haloalkynyl cyano, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, or $R^{17}$ and $R^{18}$ together with the carbon atom to which they are attached may form a 3 to 6-membered carbocyclic ring. More preferably, $R^{17}$ and $R^{18}$ are each independently hydrogen, halogen, cyano, $C_1$-$C_4$alkyl or $C_1$-$C_4$haloalkyl, even more preferably $R^{17}$ and $R^{18}$ are hydrogen, halogen or methyl, most preferably hydrogen.

Preferably, $R^{19}$ is hydrogen, $NH_2$, hydroxyl, $C_1$-$C_{12}$alkoxy, $C_1$-$C_{12}$haloalkoxy, $C_1$-$C_{12}$alkylcarbonylamino, $C_1$-$C_{12}$haloalkylcarbonylamino, $C_1$-$C_{12}$alkylamino, $C_1$-$C_{12}$haloalkylamino, $C_1$-$C_{12}$alkyl, $C_1$-$C_{12}$haloalkyl, $C_3$-$C_8$cycloalkyl, $C_3$-$C_8$halocycloalkyl, cyano, $C_1$-$C_{12}$alkenyl, $C_1$-$C_{12}$haloalkenyl, $C_2$-$C_{12}$alkynyl, $C_2$-$C_{12}$haloalkynyl, $C_1$-$C_{12}$alkylcarbonyl, $C_1$-$C_{12}$haloalkylcarbonyl, $C_1$-$C_8$alkoxycarbonyl, or $C_1$-$C_8$haloalkoxycarbonyl. More preferably, $R^{19}$ is hydrogen, $C_1$-$C_8$alkyl, $C_1$-$C_8$alkoxy, $C_1$-$C_8$alkylcarbonyl, or $C_1$-$C_8$alkoxycarbonyl, even more preferably hydrogen or methyl, most preferably $R^{19}$ is hydrogen.

Preferably $R^{20}$ is hydrogen, cyano, carbonyl, thiocarbonyl, $C_1$-$C_{12}$alkylcarbonyl, $C_1$-$C_{12}$haloalkylcarbonyl, $C_1$-$C_{12}$alkylthiocarbonyl, $C_1$-$C_{12}$haloalkylthiocarbonyl, $C_1$-$C_{12}$alkylaminocarbonyl, $C_1$-$C_{12}$alkylaminothiocarbonyl, $C_2$-$C_{24}$ (total carbon number) dialkylaminocarbonyl, $C_2$-$C_{24}$ (total carbon number) dialkylaminothiocarbonyl, $C_1$-$C_{12}$alkoxyaminocarbonyl, $C_1$-$C_{12}$alkoxyaminothiocarbonyl, $C_1$-$C_{12}$alkoxycarbonyl, $C_1$-$C_{12}$haloalkoxycarbonyl, $C_1$-$C_{12}$alkoxythiocarbonyl, $C_1$-$C_{12}$haloalkoxythiocarbonyl, $C_1$-$C_{12}$thioalkoxycarbonyl, $C_1$-$C_{12}$thioalkoxythiocarbonyl, $C_1$-$C_{12}$alkylsulfonyl, $C_1$-$C_{12}$haloalkylsulfonyl, $C_3$-$C_{12}$cycloalkylcarbonyl, $C_3$-$C_{12}$halocycloalkylcarbonyl, $C_2$-$C_{12}$alkenylcarbonyl, $C_2$-$C_{12}$haloalkenylcarbonyl, $C_2$-$C_{12}$ alkynylcarbonyl, $C_2$-$C_{12}$haloalkynylcarbonyl, $C_3$-$C_{12}$cycloalkyl-$C_1$-$C_{12}$alkylcarbonyl, $C_3$-$C_{12}$halocycloalkyl-$C_1$-$C_{12}$alkylcarbonyl, $C_2$-$C_{12}$alkylsulfenyl-$C_1$-$C_{12}$alkylcarbonyl, $C_2$-$C_{12}$haloalkylsulfenyl-$C_1$-$C_{12}$alkylcarbonyl, $C_1$-$C_{12}$alkylsulfinyl-$C_1$-$C_{12}$alkylcarbonyl, $C_1$-$C_{12}$haloalkylsulfinyl-$C_1$-$C_{12}$alkylcarbonyl, $C_1$-$C_{12}$alkylsulfonyl-$C_1$-$C_{12}$alkylcarbonyl, $C_1$-$C_{12}$haloalkylsulfonyl-$C_1$-$C_{12}$alkylcarbonyl, $C_1$-$C_{12}$alkylcarbonyl-$C_1$-$C_{12}$alkylcarbonyl, $C_1$-$C_{12}$haloalkylcarbonyl-$C_1$-$C_{12}$alkylcarbonyl, $C_3$-$C_{12}$cycloalkylaminocarbonyl, $C_2$-$C_{12}$alkenylamin- ocarbonyl, $C_2$-$C_{12}$alkynylaminocarbonyl or $C(=O)R^{21}$. More preferably, $R^{20}$ is $C_1$-$C_4$alkylcarbonyl, $C_1$-$C_4$haloalkylcarbonyl, $C_3$-$C_6$cycloalkylcarbonyl, $C_3$-$C_6$halocycloalkylcarbonyl or $C(=O)R^{21}$.

In one group of compounds $R^{19}$ and $R^{20}$ together with the nitrogen atom to which they are bound may form a 3- to 6-membered heterocyclic ring which may be substituted by one to five $R^{22}$, or may be substituted with a keto, thioketo or nitroimino group.

Preferably, $R^{21}$ is aryl or aryl substituted by one to five $R^{22}$, heterocyclyl or heterocyclyl substituted by one to five $R^{22}$, aryl-methylene or aryl-methylene wherein the aryl moiety is substituted by one to five $R^{22}$, or heterocyclyl-methylene or heterocyclyl-methylene, preferably each aryl group is a phenyl group and each heterocyclyl group is selected from pyridyl, pyridazinyl, pyrimidinyl, pyrazinyl, pyrrolyl, pyrazolyl, imidazolyl, triazolyl, tetrahydrothiophenyl, tetrazolyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxothietanyl, dioxo-thietanyl, pyrrolidinyl, tetrahydrofuranyl, [1,3]dioxolanyl, piperidinyl, piperazinyl, [1,4]dioxanyl, morpholinyl, 2,3-dihydro-benzofuranyl, benzo[1,3]dioxolanyl, and 2,3-dihydro-benzo[1,4]dioxinyl, thiazolidinyl, and 3,4-dihydro-2H-benzo[b][1,4]dioxepinyl, preferably each heterocyclyl group is selected from thiophenyl, thiazolyl, cinnolinyl and thiazolidinyl.

Preferably each $R^{22}$ is independently bromo, chloro, fluoro, cyano, nitro, oxo, methyl, ethyl, trifluoromethyl, methoxy, difluoromethoxy, trifluoromethoxy, methyl-N=, methylthio, phenyl or phenyl substituted by one to three halogen, more preferably bromo, chloro, fluoro, nitro, or methyl.

Preferably each Z is independently halogen, cyano, $C_1$-$C_4$alkyl, $C_1$-$C_4$haloalkyl, $C_1$-$C_4$alkoxy, or $C_1$-$C_4$haloalkoxy, more preferably each Z is independently hydrogen, halogen, methyl, halomethyl, methoxy or halomethoxy.

In one group of compounds of the invention
P is P1;
$A^1$, $A^2$, $A^3$ and $A^4$ are independently of each other C—H, C—$R^7$, or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$ aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;
$R^3$ is $C_1$-$C_8$haloalkyl;
$R^4$ is aryl or aryl substituted by one to five $R^{11}$, or heteroaryl or heteroaryl substituted by one to five $R^{11}$;
$R^5$ is hydrogen;
$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$ aryl or aryl substituted by one to five $R^{14}$, or heterocyclyl or heterocyclyl substituted by one to five $R^{14}$, $C_1$-$C_4$ alkoxycarbonyl-, $C_1$-$C_4$ alkenyloxycarbonyl-, $C_1$-$C_4$ alkynyloxycarbonyl-, benzyloxycarbonyl- or benzyloxycarbonyl- in which the benzyl group is optionally substituted by one to five $R^{16}$;

each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^8$ and $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^9$ and $R^{13}$ is independently halogen or $C_1$-$C_8$alkyl;

each $R^{10}$, $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;

each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;

each $R^{16}$ is independently halogen, cyano, formyl, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl;

or a salt or N-oxide thereof.

A group of preferred compounds are those wherein
$A^1$, $A^2$, $A^3$ and $A^4$ are independently of each other C—H, C—$R^7$, or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$ aryl or aryl substituted by one to five $R^{10}$, or heterocyclyl or heterocyclyl substituted by one to five $R^{10}$;
$R^3$ is $C_1$-$C_8$haloalkyl;
$R^4$ is aryl or aryl substituted by one to five $R^{11}$, or heteroaryl or heteroaryl substituted by one to five $R^{11}$;
$R^5$ is hydrogen;
$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$, aryl or aryl substituted by one to five $R^{14}$, or heterocyclyl or heterocyclyl substituted by one to five $R^{14}$;

each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^8$ and $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^9$ and $R^{13}$ is independently halogen or $C_1$-$C_8$alkyl;

each $R^{10}$, $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;

each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-.

Another group of preferred compounds are those wherein $A^1$ is C—$R^7$, $A^2$ is C—H, $A^3$ is C—H or nitrogen and $A^4$ is C—H or nitrogen;

$G^1$ is oxygen;

$R^1$ is hydrogen, methyl, ethyl, methylcarbonyl-, or methoxycarbonyl-;

$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$ aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, tetrahydrofuranyl, imidazolyl, pyrazolyl, pyrrolyl, thiazolyl, oxetanyl, thietanyl, oxo-thietanyl and dioxo-thietanyl;

$R^3$ is $C_1$-$C_8$ haloalkyl;

$R^4$ is phenyl substituted by one to three $R^{11}$;

$R^5$ is hydrogen;

$R^6$ is $C_1$-$C_8$alkyl or $C_1$-$C_8$alkyl substituted by one to five $R^{12}$, aryl-$C_1$-$C_4$alkylene- or aryl-$C_1$-$C_4$alkylene- wherein the aryl moiety is substituted by one to five $R^{14}$, heteroaryl-$C_1$-$C_4$alkylene- or heteroaryl-$C_1$-$C_4$alkylene- wherein the heteroaryl moiety is substituted by one to five $R^{14}$;

$R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkoxy-, or $C_1$-$C_8$haloalkoxy-;

each $R^8$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-;

each $R^9$ is independently chloro, fluoro or methyl;

each $R^{10}$ is independently halogen, cyano, nitro, $C_1$-$C_8$alkyl, $C_1$-$C_8$haloalkyl, $C_1$-$C_8$alkoxy-, $C_1$-$C_8$haloalkoxy-;

each $R^{11}$ is independently halogen, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-;

each $R^{12}$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-;

each $R^{14}$ is independently halogen, cyano, nitro, $C_1$-$C_8$alkyl, $C_1$-$C_8$haloalkyl, $C_1$-$C_8$alkoxy-, $C_1$-$C_8$haloalkoxy-;

Yet another group of preferred compounds are those wherein $A^1$ is C—$R^7$, $A^2$ is C—H, $A^3$ is C—H and $A^4$ is C—H;

$G^1$ is oxygen;

$I^1$ is hydrogen, methyl or ethyl;

$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$ oxo-thietanyl or oxo-thietanyl substituted by one to five $R^{10}$, or dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;

$R^3$ is chlorodifluoromethyl or trifluoromethyl;

$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl- $R^5$ is hydrogen;

$R^6$ is $C_1$-$C_8$alkyl or $C_1$-$C_8$alkyl substituted by one to five $R^{12}$, phenyl-$C_1$-$C_4$alkylene- or phenyl-$C_1$-$C_4$alkylene- wherein the phenyl moiety is substituted by one to five $R^{14}$, $R^7$ is independently bromo, chloro, fluoro, cyano, nitro, methyl, ethyl, trifluoromethyl, vinyl, methoxy, difluoromethoxy, or trifluoromethoxy;

each $R^8$ is independently bromo, chloro, fluoro, methoxy, or methylthio;

each $R^9$ is methyl;

each $R^{10}$ is independently bromo, chloro, fluoro, cyano, nitro, methyl, ethyl, trifluoromethyl, methoxy, difluoromethoxy, or trifluoromethoxy;

each $R^{12}$ is independently bromo, chloro, fluoro, methoxy, or methylthio;

each $R^{14}$ is independently bromo, chloro, fluoro, cyano, nitro, methyl, ethyl, trifluoromethyl, methoxy, difluoromethoxy, or trifluoromethoxy.

A further group of preferred compounds are those wherein $A^1$ is C—$R^7$, $A^2$ is C—H, $A^3$ is C—H and $A^4$ is C—H;

$G^1$ is oxygen;

$R^1$ is hydrogen;

$R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl or dioxo-thietanyl;

$R^3$ is trifluoromethyl;

$R^4$ is 3,5-dichloro-phenyl;

$R^5$ is hydrogen;

$R^6$ is $C_1$-$C_8$alkyl;

$R^7$ is methyl each $R^{10}$ is independently bromo, chloro, fluoro, cyano or methyl.

A further group of preferred compounds are those wherein A¹ is C—R⁷, A² is CH, A³ is CH and A⁴ is CH;

G¹ is oxygen;

R¹ is hydrogen;

R² is $C_2$-$C_6$alkyl or $C_2$-$C_6$alkyl substituted by one to three halogen atoms, $C_4$-$C_8$cycloalkyl or $C_4$-$C_8$cycloalkyl substituted by one or two methyl groups, phenyl-$C_1$-$C_2$alkylene- or phenyl-$C_1$-$C_2$alkylene- wherein the phenyl moiety is substituted by one to five $R^{10}$, pyridyl-$C_1$-$C_2$alkylene- or pyridyl-$C_1$-$C_2$alkylene- wherein the pyridyl moiety is substituted by one to four $R^{10}$, thietanyl, oxo-thietanyl or dioxo-thietanyl;

R³ is trifluoromethyl;

R⁴ is 3,5-dichloro-phenyl;

R⁵ is hydrogen;

R⁶ is $C_1$-$C_8$alkyl;

R⁷ is methyl each $R^{10}$ is independently bromo, chloro, fluoro, cyano or methyl.

In these groups of preferred compounds P is preferably P1.

In one embodiment the present invention provides compounds of formula (Ia)

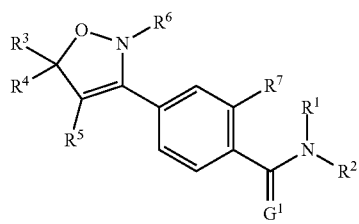

(Ia)

wherein G¹, R¹, R², R³, R⁴, R⁵, R⁶ and R⁷ are as defined for compounds of formula (I); or a salt or N-oxide thereof. The preferences for G¹, R¹, R², R³, R⁴, R⁵, R⁶ and R⁷ are the same as the preferences set out for the corresponding substituents of compounds of the formula (I).

In a further embodiment the present invention provides compounds of formula (Ib)

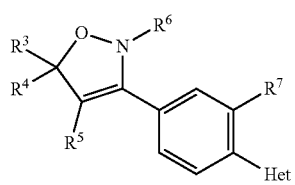

(Ib)

wherein R³, R⁴, R⁵, R⁶ and R⁷ are as defined for compounds of formula (I) and Het is selected from H1 to H9 as defined for compounds of formula I; or a salt or N-oxide thereof. The preferences for R³, R⁴, R⁵, R⁶, R⁷ and Het are the same as the preferences set out for the corresponding substituents of compounds of the formula (I).

In a further embodiment the present invention provides compounds of formula (Ic)

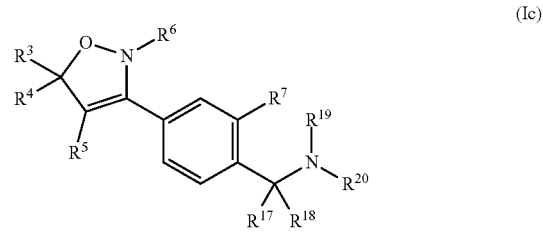

(Ic)

wherein R³, R⁴, R⁵, R⁶, R⁷, $R^{17}$, $R^{18}$, $R^{19}$ and $R^{20}$ are as defined for compounds of formula (I); or a salt or N-oxide thereof. The preferences for R³, R⁴, R⁵, R⁶, R⁷, $R^{17}$, $R^{18}$, $R^{19}$ and $R^{20}$ are the same as the preferences set out for the corresponding substituents of compounds of the formula (I).

Certain intermediates are novel and as such form a further aspect of the invention. One group of novel intermediates are compounds of formula (Int-I)

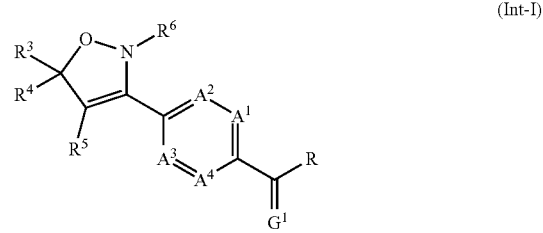

(Int-I)

wherein A¹, A², A³, A⁴, R³, R⁴, R⁵ and R⁶ are as defined for a compound of formula (I), G¹ is oxygen, and R is hydroxy, $C_1$-$C_{16}$alkoxy or halogen, such as bromo, chloro or fluoro; or a salt or N-oxide thereof. The preferences for A¹, A², A³, A⁴, R³, R⁴, R⁵ and R⁶ are the same as the preferences set out for the corresponding substituents of a compound of formula (I). Preferably R is hydroxy, $C_1$-$C_6$alkoxy or chloro.

A further group of novel intermediates are compounds of formula Int-II

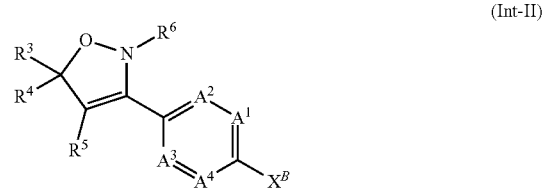

(Int-II)

wherein A¹, A², A³, A⁴, R³, R⁴, R⁵ and R⁶ are as defined for a compound of formula I, and $X^B$ is a leaving group, such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, cyano, optionally substituted $C_1$-$C_8$arylsulfonyloxy (aryl is preferably phenyl), diazonium salts (e.g. $X^B$ is —$N_2^+$ Cl⁻, —$N_2^+$ $BF_4^-$, —$N_2^+$ Br⁻, —$N_2^+$ $PF_6^-$, phosphonate esters (e.g. —OP(O)(OR)₂, wherein R is methyl or ethyl), preferably bromo, iodo, chloro, trifluoromethylsulfoxy, p-toluenesulfoxy, diazonium chloride; or a salt or N-oxide thereof. The preferences for A¹, A², A³, A⁴, R³, R⁴, R⁵ and R⁶ are the same as the preferences set out for the corresponding substituents of a compound of formula (I).

A further group of novel intermediates are compounds of formula Int-III

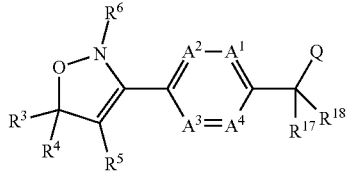

(Int-III)

wherein $A^1$, $A^2$, $A^3$, $A^4$, $R^3$, $R^4$, $R^5$, $R^6$, $R^{17}$ and $R^{18}$ are as defined for a compound or formula I, Q is phthalimidyl, hydroxy, or a leaving group such as halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. $X^B$ is —$N_2^+$ $Cl^-$, —$N_2^+$ $BF_4^-$, —$N_2^+$ $Br^-$, —$N_2^+$ $PF_6^-$), phosphonate esters (e.g. —OP(O)(OR)$_2$, wherein R is methyl or ethyl), preferably bromo, iodo, chloro, trifluoromethylsulfoxy, p-toluenesulfoxy, diazonium chloride; or a salt or N-oxide thereof. The preferences for $A^1$, $A^2$, $A^3$, $A^4$, $R^3$, $R^4$, $R^5$, $R^6$, $R^{17}$ and $R^{18}$ are the same as the preferences set out for the corresponding substituents of a compound of formula (I).

The compounds in Table 1 and 2 below illustrate the compounds of the invention.

TABLE 1

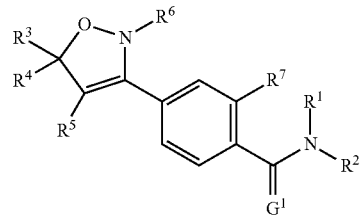

(Ia)

| Compound numbers | $R^1$ | $R^2$ |
|---|---|---|
| 1.01 | H | ethyl- |
| 1.02 | H | butyl- |
| 1.03 | H | but-2-yl- |
| 1.04 | H | 3-bromo-propyl- |
| 1.05 | H | 2,2,2-trifluoro-ethyl- |
| 1.06 | H | 3,3,3-trifluoro-propyl- |
| 1.07 | H | 2-methoxy-ethyl- |
| 1.08 | H | 1-methoxy-prop-2-yl- |
| 1.09 | H | cyclobutyl- |
| 1.10 | H | 2-methyl-cyclohex-1-yl- |
| 1.11 | H | phenyl-methyl- |
| 1.12 | H | 1-phenyl-eth-1-yl- |
| 1.13 | H | 2-phenyl-eth-1-yl- |
| 1.14 | H | (3-chloro-phenyl)-methyl- |
| 1.15 | H | (2-fluoro-phenyl)-methyl- |
| 1.16 | H | (4-methoxy-phenyl)-methyl- |
| 1.17 | H | (2-trifluoromethyl-phenyl)-methyl- |
| 1.18 | H | (2-trifluoromethoxy-phenyl)-methyl- |
| 1.19 | H | (pyrid-2-yl)-methyl- |
| 1.20 | H | (pyrid-3-yl)-methyl- |
| 1.21 | H | (2-chloro-pyrid-5-yl)-methyl- |
| 1.22 | H | (1-methyl-1H-imidazol-4-yl)-methyl- |
| 1.23 | H | (furan-2-yl)-methyl- |
| 1.24 | H | 2-(thiophen-2'-yl)-eth-1-yl- |
| 1.25 | H | 2-(indol-3'-yl)-eth-1-yl- |
| 1.26 | H | (1H-benzimidazol-2-yl)-methyl- |
| 1.27 | H | (oxetan-2-yl)-methyl- |

TABLE 1-continued (Ia)

| Compound numbers | $R^1$ | $R^2$ |
|---|---|---|
| 1.28 | H | (tetrahydrofuran-2-yl)-methyl- |
| 1.29 | H | 2-([1',3']dioxolan-2'-yl)-eth-1-yl- |
| 1.30 | H | 2-(morpholin-4'-yl)-eth-1-yl- |
| 1.31 | H | 2-(benzo[1',3']dioxol-5'-yl)-eth-1-yl- |
| 1.32 | H | (2,3-dihydro-benzo[1,4]dioxin-6-yl)-methyl- |
| 1.33 | H | 2-chloro-phenyl- |
| 1.34 | H | 3-fluoro-phenyl- |
| 1.35 | H | 2-methyl-phenyl- |
| 1.36 | H | 2-chloro-6-methyl-phenyl- |
| 1.37 | H | 2-trifluoromethyl-phenyl- |
| 1.38 | H | 2,4-dimethoxy-phenyl- |
| 1.39 | H | 3-methyl-pyrid-2-yl- |
| 1.40 | H | 1,3-dimethyl-1H-pyrazol-5-yl- |
| 1.41 | H | 4-methyl-thiazol-2-yl- |
| 1.42 | H | 5-methyl-thiadiazol-2-yl- |
| 1.43 | H | quinolin-2-yl- |
| 1.44 | H | quinolin-5-yl- |
| 1.45 | H | benzothiazol-6-yl- |
| 1.46 | H | 4-methyl-benzothiazol-2-yl- |
| 1.47 | H | thietan-3-yl- |
| 1.48 | H | 1-oxo-thietan-3-yl- |
| 1.49 | H | 1,1-dioxo-thietan-3-yl- |
| 1.50 | H | 3-methyl-thietan-3-yl- |
| 1.51 | H | N-(2,2,2-Trifluoro-ethyl)-acetamide-2-yl |
| 1.52 | H | thietan-2-yl-methyl- |
| 1.53 | H | 1-oxo-thietan-2-yl-methyl- |
| 1.54 | H | 1,1-dioxo-thietan-2-yl-methyl- |
| 1.55 | H | thietan-3-yl-methyl- |
| 1.56 | H | 1-oxo-thietan-3-yl-methyl- |
| 1.57 | H | 1,1-dioxo-thietan-3-yl-methyl- |
| 1.58 | H | thietan-3-yl-ethyl- |
| 1.59 | H | 1-oxo-thietan-3-yl-ethyl- |
| 1.60 | H | 1,1-dioxo-thietan-3-yl-ethyl- |
| 1.61 | H | 2-fluoro-cyclopropyl |
| 1.62 | H | n-Butyl |
| 1.63 | H | 2-Methoxy-1-methyl-ethyl |
| 1.64 | H | 1-Oxo-thietan-3-yl |
| 1.65 | H | 2-ethyl-isoxazolidin-3-one-4-yl |
| 1.66 | H | Dihydro-thiophen-2-one-3-yl |
| 1.67 | H | 6-Ethoxycarbonyl-cyclohex-3-enyl |
| 1.68 | H | 2-Benzylsulfanyl-ethyl |
| 1.69 | H | 4-Methanesulfonyl-benzyl |
| 1.70 | H | N',N'-Dimethylamino-ethyl |
| 1.71 | H | sec-Butyl |
| 1.72 | H | Butan-1-ol-2-yl |
| 1.73 | H | 2,2-Difluoro-ethyl |
| 1.74 | H | Ethynyl-cyclohexyl |
| 1.75 | H | 2-Morpholin-4-yl-ethyl |
| 1.76 | H | 3-Pyrrolidin-1-yl-propyl |
| 1.77 | H | 3-Piperidin-1-yl-propyl |
| 1.78 | H | [3-(4-Chloro-phenyl)-isoxazol-5-yl]-methyl |
| 1.79 | H | Phenethyl |
| 1.80 | H | 1,2,2,6,6-Pentamethyl-piperidin-4-yl |
| 1.81 | H | 2-Phenoxy-ethyl |
| 1.82 | H | 3-Chloro-benzyl |
| 1.83 | H | 2-Acetylamino-ethyl |
| 1.84 | H | 4-Pyrazol-1-yl-benzyl |
| 1.85 | H | 2-Methylsulfanyl-ethyl |
| 1.86 | H | 2-Piperidin-1-yl-benzyl |
| 1.87 | H | 4-Phenoxy-benzyl |
| 1.88 | H | (6-Chloro-pyridin-3-yl)-methyl |
| 1.89 | H | 1-Benzyl-pyrrolidin-3-yl |
| 1.90 | H | 2-(4-Benzyl-piperazin-1-yl)-ethyl |
| 1.91 | H | Furan-2-yl-methyl |

TABLE 1-continued (Ia)

| Compound numbers | R¹ | R² |
|---|---|---|
| 1.92 | H | 1H-Indazol-5-yl |
| 1.93 | H | 4-Pyrrol-1-yl-phenyl |
| 1.94 | H | 4-Piperidin-1-yl-phenyl |
| 1.95 | H | 2-Methylsulfanyl-phenyl |
| 1.96 | H | 4-Methyl-2-oxo-2H-chromen-7-yl |
| 1.97 | H | 4-Dimethylsulfamoyl-phenyl |
| 1.98 | H | 2,5-Dimethyl-1H-pyrazol-3-yl |
| 1.99 | H | 5-Methylsulfanyl-1H-[1,2,4]triazol-3-yl |
| 1.100 | H | 4-Hydroxy-6-methyl-pyrimidin-2-yl |
| 1.101 | H | Quinolin-2-yl |
| 1.102 | H | 5-Methyl-3-phenyl-isoxazol-4-yl |
| 1.103 | H | 9H-Purin-6-yl |
| 1.104 | H | 5-Acetyl-4-methyl-thiazol-2-yl |
| 1.105 | H | 4-Methyl-benzothiazol-2-yl |
| 1.106 | H | 5-Methyl-[1,3,4]thiadiazol-2-yl |
| 1.107 | H | 4,6-Dimethyl-2H-pyrazolo[3,4-b]pyridin-3-yl |
| 1.108 | H | 3-(2,2,2-Trifluoro-ethoxyimino)-cyclobutyl |
| 1.109 | H | 2-Thietan-3-yl-ethyl |
| 1.110 | H | 2-(1,1-Dioxo-thietan-3-yl)-ethyl |
| 1.112 | H | 3-Oxo-2-(2,2,2-trifluoro-ethyl)-isoxazolidin-4-yl |
| 1.113 | H | [structure: C(CH₃)=N–O–CH₃] |
| 1.114 | H | [structure: C(CH₃)=N–O–CH₂CH₃] |
| 1.115 | H | 2-(2,2,2-trifluoro-ethyl)-isoxazolidin-3-one-4-yl |
| 1.116 | H | 2-(2,2-Difluoro-ethyl)-isoxazolidin-3-one-4-yl |
| 1.117 | H | 2-(2-Fluoro-ethyl)-isoxazolidin-3-one-4-yl |

Table 1 provides 117 compounds of formula (Ia) wherein G¹ is oxygen, R³ is trifluoromethyl, R⁴ is 3,5-dichloro-phenyl-, R⁵ is hydrogen, R⁶ and R⁷ are both methyl, and R¹ and R² have the values listed in the table below.

TABLE 2

(Id)

| No. | R⁴ | R⁷ | P |
|---|---|---|---|
| 1 | 3,5-dichloro-phenyl | CN | 1,2,4-triazol-1-yl |
| 2 | 3,5-dichloro-phenyl | CN | 4-cyano-pyrazol-1-yl |
| 3 | 3,5-dichloro-phenyl | CN | 4-fluoro-pyrazol-1-yl |
| 4 | 3,5-dichloro-phenyl | CN | 4-chloro-pyrazol-1-yl |
| 5 | 3,5-dichloro-phenyl | H | –CH(CH₃)–NH–C(O)–cyclopropyl |
| 6 | 3,5-dichloro-phenyl | H | –CH(CH₃)–NH–C(O)–CH₂CF₃ |
| 7 | 3,5-dichloro-phenyl | Cl | –CH₂–NH–C(O)–CH₂–S–CH₃ |
| 8 | 3,5-dichloro-phenyl | Cl | –CH₂–NH–C(O)–CH₂–S(O)–CH₃ |
| 9 | 3,5-dichloro-phenyl | Cl | –CH₂–NH–C(O)–CH₂–S(O)₂–CH₃ |
| 10 | 3,5-dichloro-phenyl | Cl | –CH₂–NH–C(O)–CH(CH₃)₂ |
| 11 | 3,5-dichloro-phenyl | Cl | –CH₂–NH–C(O)–CH₂CH₃ |

TABLE 2-continued (Id)

[Structure: isoxazoline with R3, R4, R5 substituents at 5-position, R6 on N, phenyl ring with R7 and P substituents]

| No. | R⁴ | R⁷ | P |
|---|---|---|---|
| 12 | 3,5-dichloro-phenyl | Cl | -CH₂-NH-C(O)-CH₂-CF₃ |
| 13 | 3,5-dichloro-phenyl | Cl | -CH₂-NH-C(O)-CH₃ |
| 14 | 3,5-dichloro-phenyl | Cl | -CH₂-NH-C(O)-cyclopropyl |
| 15 | 3,5-dichloro-phenyl | Br | -CH₂-NH-C(O)-CH₂-S-CH₃ |
| 16 | 3,5-dichloro-phenyl | Br | -CH₂-NH-C(O)-CH₂-S(O)-CH₃ |
| 17 | 3,5-dichloro-phenyl | Br | -CH₂-NH-C(O)-CH₂-S(O)₂-CH₃ |
| 18 | 3,5-dichloro-phenyl | Br | -CH₂-NH-C(O)-CH(CH₃)₂ |
| 19 | 3,5-dichloro-phenyl | Br | -CH₂-NH-C(O)-CH₂CH₃ |
| 20 | 3,5-dichloro-phenyl | Br | -CH₂-NH-C(O)-CH₂-CF₃ |
| 21 | 3,5-dichloro-phenyl | Br | -CH₂-NH-C(O)-CH₃ |
| 22 | 3,5-dichloro-phenyl | Br | -CH₂-NH-C(O)-cyclopropyl |
| 23 | 3,5-dichloro-phenyl | CF₃ | -CH₂-NH-C(O)-CH₂-S-CH₃ |
| 24 | 3,5-dichloro-phenyl | CF₃ | -CH₂-NH-C(O)-CH₂-S(O)-CH₃ |
| 25 | 3,5-dichloro-phenyl | CF₃ | -CH₂-NH-C(O)-CH₂-S(O)₂-CH₃ |
| 26 | 3,5-dichloro-phenyl | CF₃ | -CH₂-NH-C(O)-CH(CH₃)₂ |
| 27 | 3,5-dichloro-phenyl | CF₃ | -CH₂-NH-C(O)-CH₂CH₃ |
| 28 | 3,5-dichloro-phenyl | CF₃ | -CH₂-NH-C(O)-CH₂-CF₃ |
| 29 | 3,5-dichloro-phenyl | CF₃ | -CH₂-NH-C(O)-CH₃ |
| 30 | 3,5-dichloro-phenyl | CF₃ | -CH₂-NH-C(O)-cyclopropyl |
| 31 | 3,5-Bis trifluoromethyl-phenyl | CN | -CH₂-(1,2,4-triazol-1-yl) |

TABLE 2-continued (Id)

| No. | R⁴ | R⁷ | P |
|---|---|---|---|
| 32 | 3,5-Bis trifluoro methyl-phenyl | CN | 1-(4-cyano)pyrazolyl |
| 33 | 3,5-Bis trifluoro methyl-phenyl | CN | 1-(4-fluoro)pyrazolyl |
| 34 | 3,5-Bis trifluoro methyl-phenyl | CN | 1-(4-chloro)pyrazolyl |
| 35 | 3,5-Bis trifluoro methyl-phenyl | H | —CH(CH₃)NHC(O)-cyclopropyl |
| 36 | 3,5-Bis trifluoro methyl-phenyl | H | —CH(CH₃)NHC(O)CH₂CF₃ |
| 37 | 3,5-Bis trifluoro methyl-phenyl | Cl | —CH₂NHC(O)CH₂SCH₃ |
| 38 | 3,5-Bis trifluoro methyl-phenyl | Cl | —CH₂NHC(O)CH₂S(O)CH₃ |
| 39 | 3,5-Bis trifluoro methyl-phenyl | Cl | —CH₂NHC(O)CH₂S(O)₂CH₃ |
| 40 | 3,5-Bis trifluoro methyl-phenyl | Cl | —CH₂NHC(O)CH(CH₃)₂ |
| 41 | 3,5-Bis trifluoro methyl-phenyl | Cl | —CH₂NHC(O)CH₂CH₃ |
| 42 | 3,5-Bis trifluoro methyl-phenyl | Cl | —CH₂NHC(O)CH₂CF₃ |
| 43 | 3,5-Bis trifluoro methyl-phenyl | Cl | —CH₂NHC(O)CH₃ |
| 44 | 3,5-Bis trifluoro methyl-phenyl | Cl | —CH₂NHC(O)-cyclopropyl |
| 45 | 3,5-Bis trifluoro methyl-phenyl | Br | —CH₂NHC(O)CH₂SCH₃ |
| 46 | 3,5-Bis trifluoro methyl-phenyl | Br | —CH₂NHC(O)CH₂S(O)CH₃ |
| 47 | 3,5-Bis trifluoro methyl-phenyl | Br | —CH₂NHC(O)CH₂S(O)₂CH₃ |
| 48 | 3,5-Bis trifluoro methyl-phenyl | Br | —CH₂NHC(O)CH(CH₃)₂ |
| 49 | 3,5-Bis trifluoro methyl-phenyl | Br | —CH₂NHC(O)CH₂CH₃ |
| 50 | 3,5-Bis trifluoro methyl-phenyl | Br | —CH₂NHC(O)CH₂CF₃ |
| 51 | 3,5-Bis trifluoro methyl-phenyl | Br | —CH₂NHC(O)CH₃ |

TABLE 2-continued (Id)

| No. | R⁴ | R⁷ | P |
|---|---|---|---|
| 52 | 3,5-Bis trifluoro methyl-phenyl | Br | -CH₂-NH-C(O)-cyclopropyl |
| 53 | 3,5-Bis trifluoro methyl-phenyl | CF₃ | -CH₂-NH-C(O)-CH₂-S-CH₃ |
| 54 | 3,5-Bis trifluoro methyl-phenyl | CF₃ | -CH₂-NH-C(O)-CH₂-S(O)-CH₃ |
| 55 | 3,5-Bis trifluoro methyl-phenyl | CF₃ | -CH₂-NH-C(O)-CH₂-S(O)₂-CH₃ |
| 56 | 3,5-Bis trifluoro methyl-phenyl | CF₃ | -CH₂-NH-C(O)-CH(CH₃)₂ |
| 57 | 3,5-Bis trifluoro methyl-phenyl | CF₃ | -CH₂-NH-C(O)-CH₂CH₃ |
| 58 | 3,5-Bis trifluoro methyl-phenyl | CF₃ | -CH₂-NH-C(O)-CH₂-CF₃ |
| 59 | 3,5-Bis trifluoro methyl-phenyl | CF₃ | -CH(CH₃)-NH-C(O)-CH₃ |
| 60 | 3,5-Bis trifluoro methyl-phenyl | CF₃ | -CH(CH₃)-NH-C(O)-cyclopropyl |
| 61 | 3,4,5-Trichloro-phenyl | CN | 1,2,4-triazol-1-yl |
| 62 | 3,4,5-Trichloro-phenyl | CN | 4-cyano-pyrazol-1-yl |
| 63 | 3,4,5-Trichloro-phenyl | CN | 4-fluoro-pyrazol-1-yl |
| 64 | 3,4,5-Trichloro-phenyl | CN | 4-chloro-pyrazol-1-yl |
| 65 | 3,4,5-Trichloro-phenyl | H | -CH(CH₃)-NH-C(O)-cyclopropyl |
| 66 | 3,4,5-Trichloro-phenyl | H | -CH(CH₃)-NH-C(O)-CH₂-CF₃ |
| 67 | 3,4,5-Trichloro-phenyl | Cl | -CH₂-NH-C(O)-CH₂-S-CH₃ |
| 68 | 3,4,5-Trichloro-phenyl | Cl | -CH₂-NH-C(O)-CH₂-S(O)-CH₃ |
| 69 | 3,4,5-Trichloro-phenyl | Cl | -CH₂-NH-C(O)-CH₂-S(O)₂-CH₃ |
| 70 | 3,4,5-Trichloro-phenyl | Cl | -CH₂-NH-C(O)-CH(CH₃)₂ |
| 71 | 3,4,5-Trichloro-phenyl | Cl | -CH₂-NH-C(O)-CH₂CH₃ |

TABLE 2-continued (Id)

| No. | R⁴ | R⁷ | P |
|---|---|---|---|
| 72 | 3,4,5-Trichloro-phenyl | Cl | -CH₂-NH-C(O)-CF₃ |
| 73 | 3,4,5-Trichloro-phenyl | Cl | -CH₂-NH-C(O)-CH₃ |
| 74 | 3,4,5-Trichloro-phenyl | Cl | -CH₂-NH-C(O)-cyclopropyl |
| 75 | 3,4,5-Trichloro-phenyl | Br | -CH₂-NH-C(O)-CH₂-S-CH₃ |
| 76 | 3,4,5-Trichloro-phenyl | Br | -CH₂-NH-C(O)-CH₂-S(O)-CH₃ |
| 77 | 3,4,5-Trichloro-phenyl | Br | -CH₂-NH-C(O)-CH₂-S(O)₂-CH₃ |
| 78 | 3,4,5-Trichloro-phenyl | Br | -CH₂-NH-C(O)-CH(CH₃)₂ |
| 79 | 3,4,5-Trichloro-phenyl | Br | -CH₂-NH-C(O)-CH₂CH₃ |
| 80 | 3,4,5-Trichloro-phenyl | Br | -CH₂-NH-C(O)-CH₂-CF₃ |
| 81 | 3,4,5-Trichloro-phenyl | Br | -CH₂-NH-C(O)-CH₃ |
| 82 | 3,4,5-Trichloro-phenyl | Br | -CH₂-NH-C(O)-cyclopropyl |
| 83 | 3,4,5-Trichloro-phenyl | CF₃ | -CH₂-NH-C(O)-CH₂-S-CH₃ |
| 84 | 3,4,5-Trichloro-phenyl | CF₃ | -CH₂-NH-C(O)-CH₂-S(O)-CH₃ |
| 85 | 3,4,5-Trichloro-phenyl | CF₃ | -CH₂-NH-C(O)-CH₂-S(O)₂-CH₃ |
| 86 | 3,4,5-Trichloro-phenyl | CF₃ | -CH₂-NH-C(O)-CH(CH₃)₂ |
| 87 | 3,4,5-Trichloro-phenyl | CF₃ | -CH₂-NH-C(O)-CH₂CH₃ |
| 88 | 3,4,5-Trichloro-phenyl | CF₃ | -CH₂-NH-C(O)-CH₂-CF₃ |
| 89 | 3,4,5-Trichloro-phenyl | CF₃ | -CH₂-NH-C(O)-CH₃ |
| 90 | 3,4,5-Trichloro-phenyl | CF₃ | -CH₂-NH-C(O)-cyclopropyl |
| 91 | 3,5-dichloro-4-fluoro-phenyl | CN | -CH₂-(1,2,4-triazol-1-yl) |

TABLE 2-continued (Id)

| No. | R⁴ | R⁷ | P |
|---|---|---|---|
| 92 | 3,5-dichloro-4-fluoro-phenyl | CN | 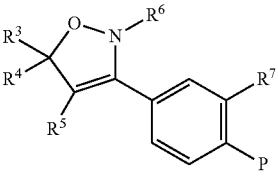 |
| 93 | 3,5-dichloro-4-fluoro-phenyl | CN | 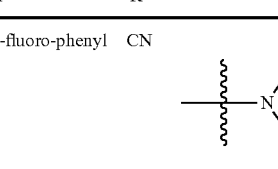 |
| 94 | 3,5-dichloro-4-fluoro-phenyl | CN | 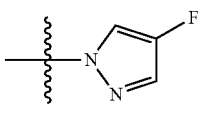 [SMILES: *n1cc(F)cn1] |
| 95 | 3,5-dichloro-4-fluoro-phenyl | H | 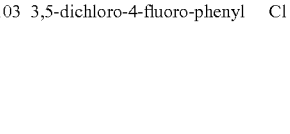 |
| 96 | 3,5-dichloro-4-fluoro-phenyl | H | 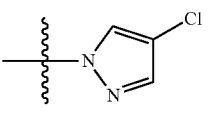 [SMILES: *n1cc(Cl)cn1] |
| 97 | 3,5-dichloro-4-fluoro-phenyl | Cl | 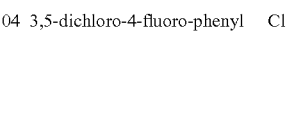 |
| 98 | 3,5-dichloro-4-fluoro-phenyl | Cl | 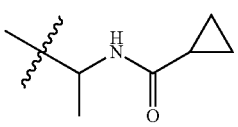 [SMILES: *C(C)NC(=O)C1CC1] |
| 99 | 3,5-dichloro-4-fluoro-phenyl | Cl | 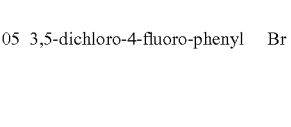 |
| 100 | 3,5-dichloro-4-fluoro-phenyl | Cl | 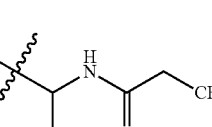 |
| 101 | 3,5-dichloro-4-fluoro-phenyl | Cl | 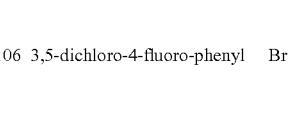 |
| 102 | 3,5-dichloro-4-fluoro-phenyl | Cl | 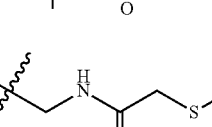 |
| 103 | 3,5-dichloro-4-fluoro-phenyl | Cl | 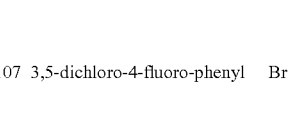 |
| 104 | 3,5-dichloro-4-fluoro-phenyl | Cl | 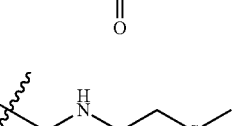 |
| 105 | 3,5-dichloro-4-fluoro-phenyl | Br | 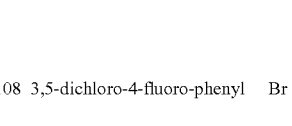 |
| 106 | 3,5-dichloro-4-fluoro-phenyl | Br | 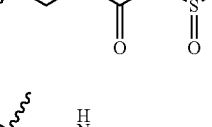 |
| 107 | 3,5-dichloro-4-fluoro-phenyl | Br | 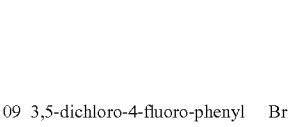 |
| 108 | 3,5-dichloro-4-fluoro-phenyl | Br | 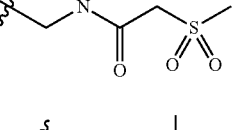 |
| 109 | 3,5-dichloro-4-fluoro-phenyl | Br |  |
| 110 | 3,5-dichloro-4-fluoro-phenyl | Br | 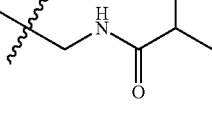 |
| 111 | 3,5-dichloro-4-fluoro-phenyl | Br | 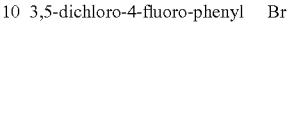 |

TABLE 2-continued (Id)

| No. | R⁴ | R⁷ | P |
|---|---|---|---|
| 112 | 3,5-dichloro-4-fluoro-phenyl | Br | -CH₂-NH-C(O)-cyclopropyl |
| 113 | 3,5-dichloro-4-fluoro-phenyl | CF₃ | -CH₂-NH-C(O)-CH₂-S-CH₃ |
| 114 | 3,5-dichloro-4-fluoro-phenyl | CF₃ | -CH₂-NH-C(O)-CH₂-S(O)-CH₃ |
| 115 | 3,5-dichloro-4-fluoro-phenyl | CF₃ | -CH₂-NH-C(O)-CH₂-S(O)₂-CH₃ |
| 116 | 3,5-dichloro-4-fluoro-phenyl | CF₃ | -CH₂-NH-C(O)-CH(CH₃)₂ |
| 117 | 3,5-dichloro-4-fluoro-phenyl | CF₃ | -CH₂-NH-C(O)-CH₂CH₃ |
| 118 | 3,5-dichloro-4-fluoro-phenyl | CF₃ | -CH₂-NH-C(O)-CH₂-CF₃ |
| 119 | 3,5-dichloro-4-fluoro-phenyl | CF₃ | -CH₂-NH-C(O)-CH₃ |
| 120 | 3,5-dichloro-4-fluoro-phenyl | CF₃ | -CH₂-NH-C(O)-cyclopropyl |
| 121 | 3-chloro-5-trifluoromethyl-phenyl | CN | 1,2,4-triazol-1-yl |
| 122 | 3-chloro-5-trifluoromethyl-phenyl | CN | 4-cyano-pyrazol-1-yl |
| 123 | 3-chloro-5-trifluoromethyl-phenyl | CN | 4-fluoro-pyrazol-1-yl |
| 124 | 3-chloro-5-trifluoromethyl-phenyl | CN | 4-chloro-pyrazol-1-yl |
| 125 | 3-chloro-5-trifluoromethyl-phenyl | H | -CH(CH₃)-NH-C(O)-cyclopropyl |
| 126 | 3-chloro-5-trifluoromethyl-phenyl | H | -CH(CH₃)-NH-C(O)-CH₂-CF₃ |
| 127 | 3-chloro-5-trifluoromethyl-phenyl | Cl | -CH₂-NH-C(O)-CH₂-S-CH₃ |
| 128 | 3-chloro-5-trifluoromethyl-phenyl | Cl | -CH₂-NH-C(O)-CH₂-S(O)-CH₃ |
| 129 | 3-chloro-5-trifluoromethyl-phenyl | Cl | -CH₂-NH-C(O)-CH₂-S(O)₂-CH₃ |
| 130 | 3-chloro-5-trifluoromethyl-phenyl | Cl | -CH₂-NH-C(O)-CH(CH₃)₂ |
| 131 | 3-chloro-5-trifluoromethyl-phenyl | Cl | -CH₂-NH-C(O)-CH₂CH₃ |

TABLE 2-continued (Id)

| No. | R⁴ | R⁷ | P |
|---|---|---|---|
| 132 | 3-chloro-5-trifluoromethyl-phenyl | Cl | -CH₂-NH-C(O)-CF₃ |
| 133 | 3-chloro-5-trifluoromethyl-phenyl | Cl | -CH₂-NH-C(O)-CH₃ |
| 134 | 3-chloro-5-trifluoromethyl-phenyl | Cl | -CH₂-NH-C(O)-cyclopropyl |
| 135 | 3-chloro-5-trifluoromethyl-phenyl | Br | -CH₂-NH-C(O)-CH₂-S-CH₃ |
| 136 | 3-chloro-5-trifluoromethyl-phenyl | Br | -CH₂-NH-C(O)-CH₂-S(O)-CH₃ |
| 137 | 3-chloro-5-trifluoromethyl-phenyl | Br | -CH₂-NH-C(O)-CH₂-S(O)₂-CH₃ |
| 138 | 3-chloro-5-trifluoromethyl-phenyl | Br | -CH₂-NH-C(O)-CH(CH₃)₂ |
| 139 | 3-chloro-5-trifluoromethyl-phenyl | Br | -CH₂-NH-C(O)-CH₂CH₃ |
| 140 | 3-chloro-5-trifluoromethyl-phenyl | Br | -CH₂-NH-C(O)-CH₂-CF₃ |
| 141 | 3-chloro-5-trifluoromethyl-phenyl | Br | -CH₂-NH-C(O)-CH₃ |
| 142 | 3-chloro-5-trifluoromethyl-phenyl | Br | -CH₂-NH-C(O)-cyclopropyl |
| 143 | 3-chloro-5-trifluoromethyl-phenyl | CF₃ | -CH₂-NH-C(O)-CH₂-S-CH₃ |
| 144 | 3-chloro-5-trifluoromethyl-phenyl | CF₃ | -CH₂-NH-C(O)-CH₂-S(O)-CH₃ |
| 145 | 3-chloro-5-trifluoromethyl-phenyl | CF₃ | -CH₂-NH-C(O)-CH₂-S(O)₂-CH₃ |
| 146 | 3-chloro-5-trifluoromethyl-phenyl | CF₃ | -CH₂-NH-C(O)-CH(CH₃)₂ |
| 147 | 3-chloro-5-trifluoromethyl-phenyl | CF₃ | -CH₂-NH-C(O)-CH₂CH₃ |
| 148 | 3-chloro-5-trifluoromethyl-phenyl | CF₃ | -CH₂-NH-C(O)-CH₂-CF₃ |
| 149 | 3-chloro-5-trifluoromethyl-phenyl | CF₃ | -CH₂-NH-C(O)-CH₃ |
| 150 | 3-chloro-5-trifluoromethyl-phenyl | CF₃ | -CH₂-NH-C(O)-cyclopropyl |
| 151 | 3-chloro-5-bromo-phenyl | CN | -CH₂-(1,2,4-triazol-1-yl) |

TABLE 2-continued

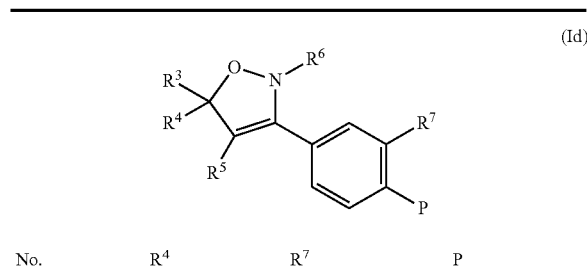

(Id)

| No. | R⁴ | R⁷ | P |
|---|---|---|---|
| 152 | 3-chloro-5-bromo-phenyl | CN | 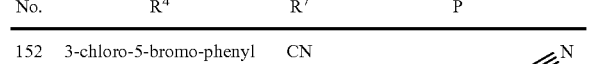 |
| 153 | 3-chloro-5-bromo-phenyl | CN |  |
| 154 | 3-chloro-5-bromo-phenyl | CN | 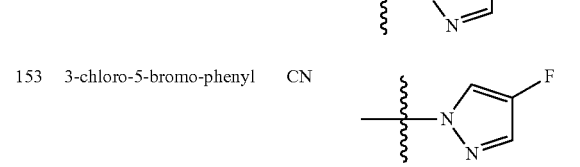 |
| 155 | 3-chloro-5-bromo-phenyl | H | 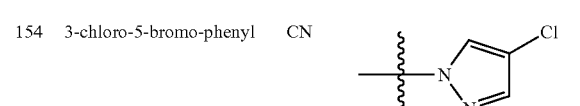 |
| 156 | 3-chloro-5-bromo-phenyl | H | 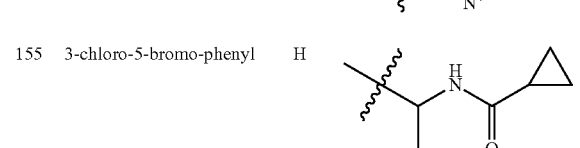 |
| 157 | 3-chloro-5-bromo-phenyl | Cl | 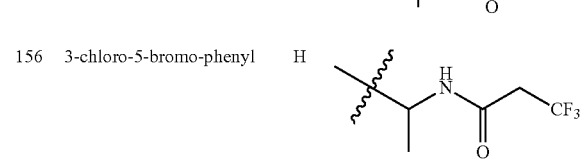 |
| 158 | 3-chloro-5-bromo-phenyl | Cl | 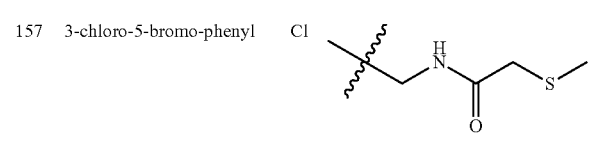 |
| 159 | 3-chloro-5-bromo-phenyl | Cl | 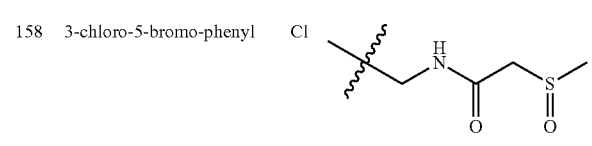 |
| 160 | 3-chloro-5-bromo-phenyl | Cl | 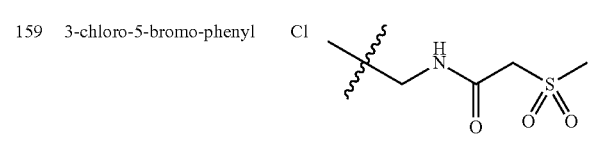 |
| 161 | 3-chloro-5-bromo-phenyl | Cl | 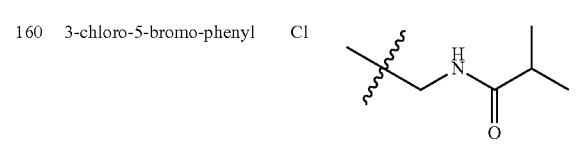 |

TABLE 2-continued

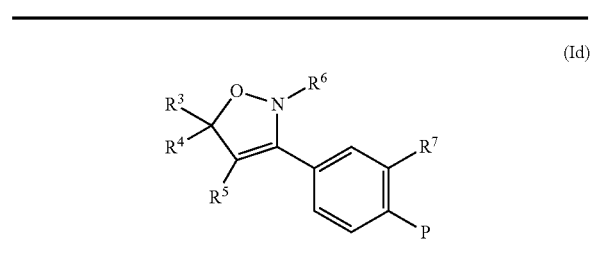

(Id)

| No. | R⁴ | R⁷ | P |
|---|---|---|---|
| 162 | 3-chloro-5-bromo-phenyl | Cl | 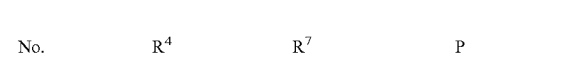 |
| 163 | 3-chloro-5-bromo-phenyl | Cl | 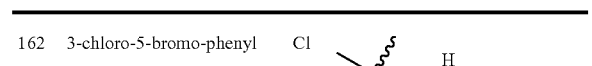 |
| 164 | 3-chloro-5-bromo-phenyl | Cl | 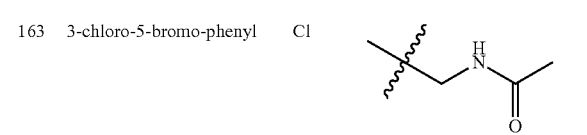 |
| 165 | 3-chloro-5-bromo-phenyl | Br | 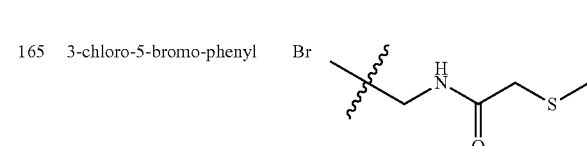 |
| 166 | 3-chloro-5-bromo-phenyl | Br | 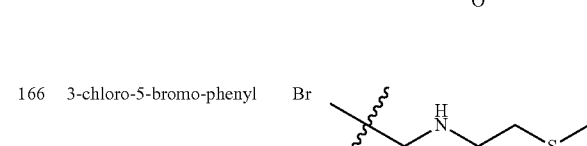 |
| 167 | 3-chloro-5-bromo-phenyl | Br | 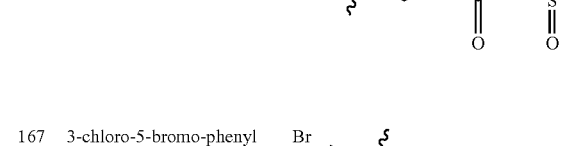 |
| 168 | 3-chloro-5-bromo-phenyl | Br | 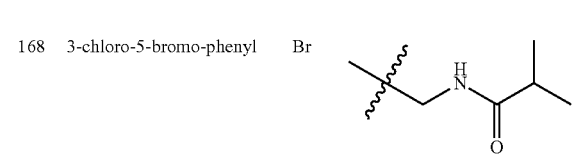 |

TABLE 2-continued (Id)

| No. | R⁴ | R⁷ | P |
|---|---|---|---|
| 169 | 3-chloro-5-bromo-phenyl | Br | -CH₂-NH-C(O)-CH₂CH₃ |
| 170 | 3-chloro-5-bromo-phenyl | Br | -CH₂-NH-C(O)-CH₂-CF₃ |
| 171 | 3-chloro-5-bromo-phenyl | Br | -CH₂-NH-C(O)-CH₃ |
| 172 | 3-chloro-5-bromo-phenyl | Br | -CH₂-NH-C(O)-cyclopropyl |
| 173 | 3-chloro-5-bromo-phenyl | CF₃ | -CH₂-NH-C(O)-CH₂-S-CH₃ |
| 174 | 3-chloro-5-bromo-phenyl | CF₃ | -CH₂-NH-C(O)-CH₂-S(O)-CH₃ |
| 175 | 3-chloro-5-bromo-phenyl | CF₃ | -CH₂-NH-C(O)-CH₂-S(O)₂-CH₃ |
| 176 | 3-chloro-5-bromo-phenyl | CF₃ | -CH₂-NH-C(O)-CH(CH₃)₂ |
| 177 | 3-chloro-5-bromo-phenyl | CF₃ | -CH₂-NH-C(O)-CH₂CH₃ |
| 178 | 3-chloro-5-bromo-phenyl | CF₃ | -CH₂-NH-C(O)-CH₂-CF₃ |
| 179 | 3-chloro-5-bromo-phenyl | CF₃ | -CH₂-NH-C(O)-CH₃ |
| 180 | 3-chloro-5-bromo-phenyl | CF₃ | -CH₂-NH-C(O)-cyclopropyl |

Table 2 provides 180 compounds of formula (Id) wherein R³ is trifluoromethyl, R⁵ is hydrogen, R⁶ is methyl, and R⁴, R⁷ and P have the values listed in the table below.

Compounds of formula I include at least one chiral centre and may exist as compounds of formula I* or compounds of formula I**.

Compounds of formula I*:

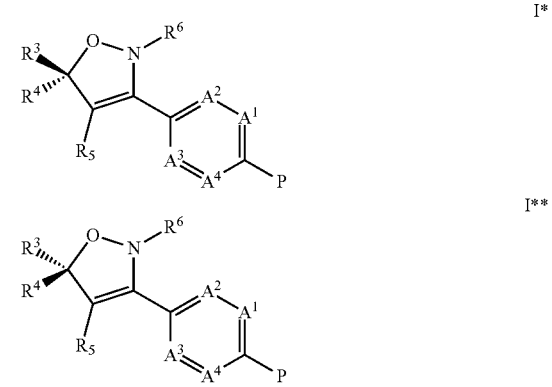

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimerically) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred.

The compounds of the invention may be made by a variety of methods as shown in Schemes 1 to 21.

Scheme 1
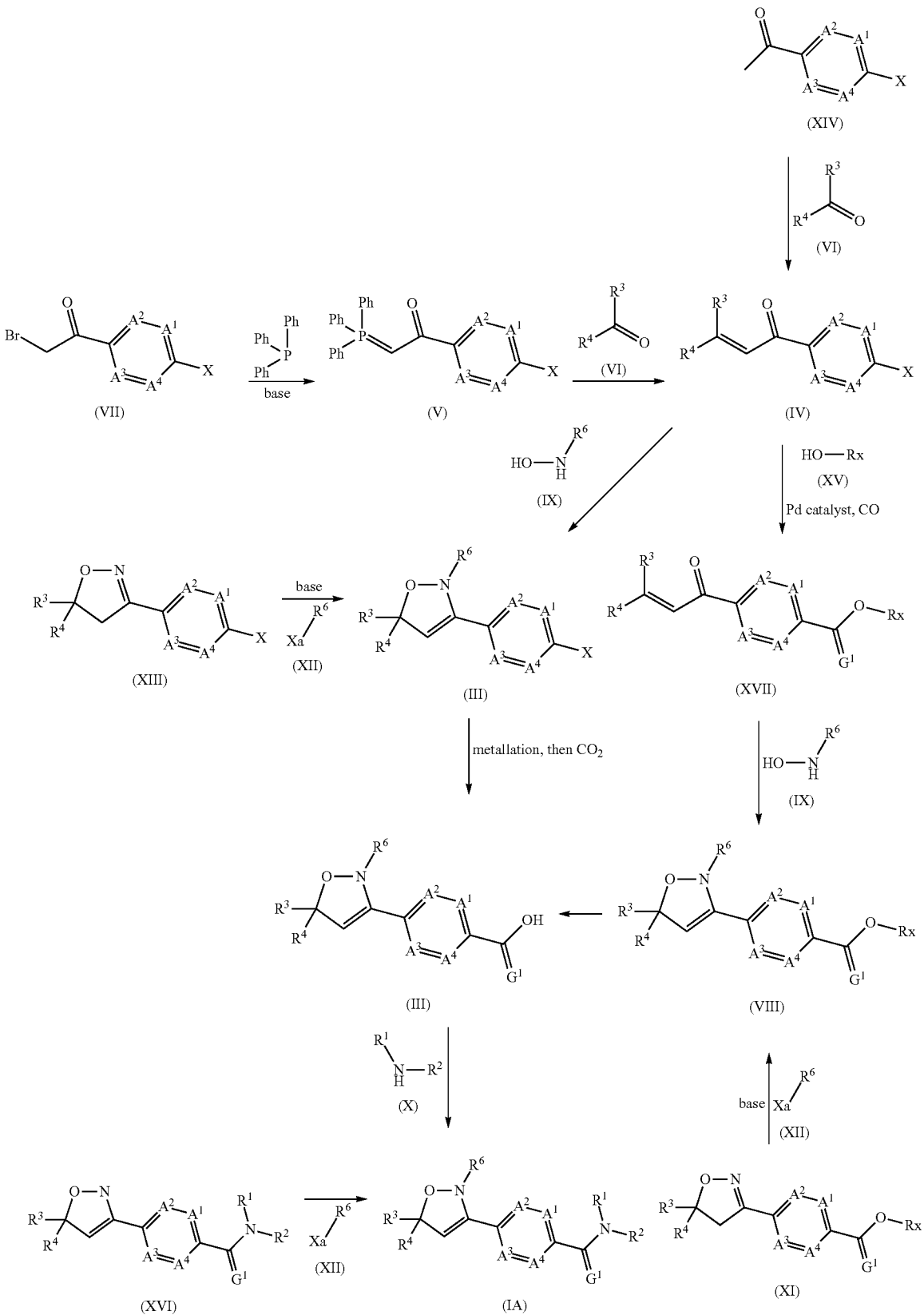

Scheme 2

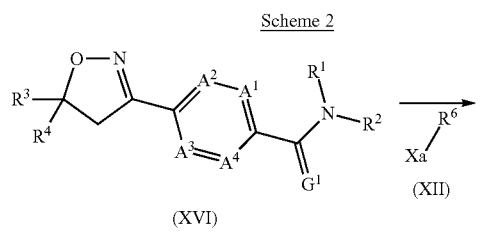

(XVI)

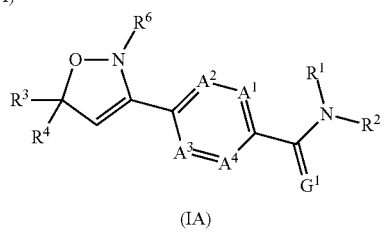

(IA)

1) Compounds of formula (IA), wherein $R^6$ is other than hydrogen, can be made by treatment of a compound of formula (XVI) with base, such as lithium diisopropylamine ("LDA"), followed by the addition of a compound (XII) wherein $X_a$ is a leaving group, for example an alkylating or an acylating agent, in the presence of a suitable solvent, such as tetrahydrofuran. Suitable alkylating agents are, for example, alkyl halides, such as methyl iodide (Me-I), for making a compound (IA) where $R^6$ is $C_1$-$C_8$alkyl, in particular allyl, and acylating agents such as methyl chloroformate, ethyl chloroformate for making a compound (IA) where $R^6$ is methoxycarbonyl or ethoxycarbonyl. The reaction is carried out at a temperature of from $-120°$ C. to $+30°$ C., preferably from $-100°$ C. to $0°$ C. Alternatively, compounds of formula (I), wherein $R^6$ is other than hydrogen, can be made by treatment of a compound of formula (XVI) with a strong alkylating agent, such as trimethyloxonium tetrafluoroborate, in a suitable solvent, for instance 1,2-dichloroethane.

Scheme 3

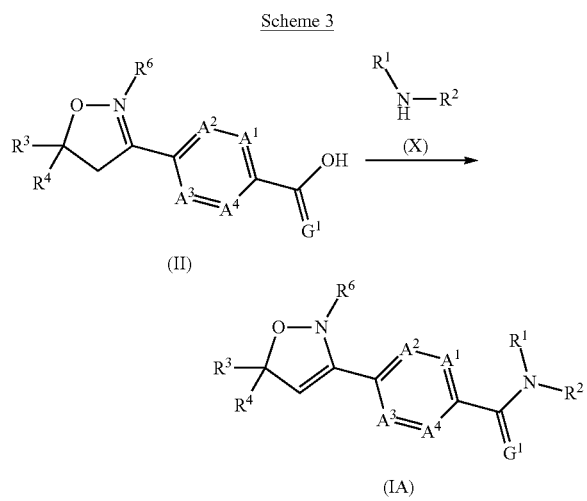

2) Compounds of formula (IA) can be made by treatment of a compound of formula (II) with a compound of formula (X) and a dehydrating reagent. Alternatively, carboxylic acid (IA) is transformed to an activated derivative, such as an acid chloride, for instance by treatment with thionyl chloride, or a mixed anhydride, for instance by treatment with ethyl chloroformate, and the activated derivative is reacted with a compound of formula (X), optionally in the presence of a base, and in a suitable solvent, such as, for instance, tetrahydrofuran. The reaction is carried out at a temperature of from $-120°$ C. to $+130°$ C., preferably from $-100°$ C. to $100°$ C.

Scheme 4

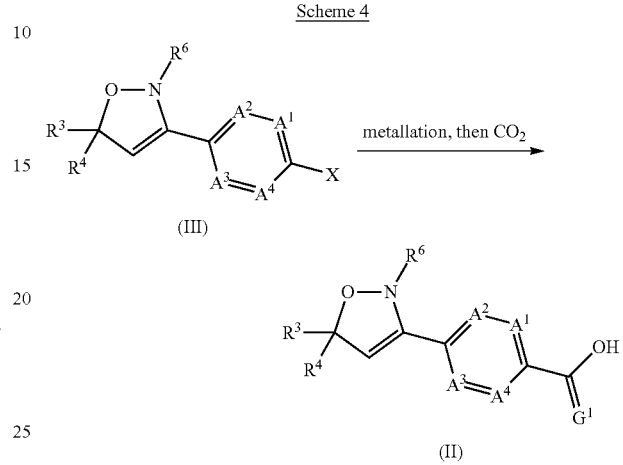

(III)

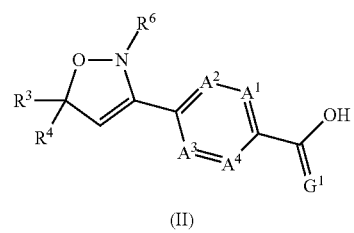

(II)

3) Compounds of formula (II), wherein $G^1$ is oxygen, can be made by treatment of a compound of formula (III), wherein X is a halogen, for instance bromine, with a metallating agent, such as a metal, for instance magnesium, or an organometallic compound, for instance butyllithium, followed by the treatment with carbon dioxide. The reaction is carried out at a temperature of from $-120°$ C. to $+130°$ C., preferably from $-100°$ C. to $100°$ C.

Scheme 5

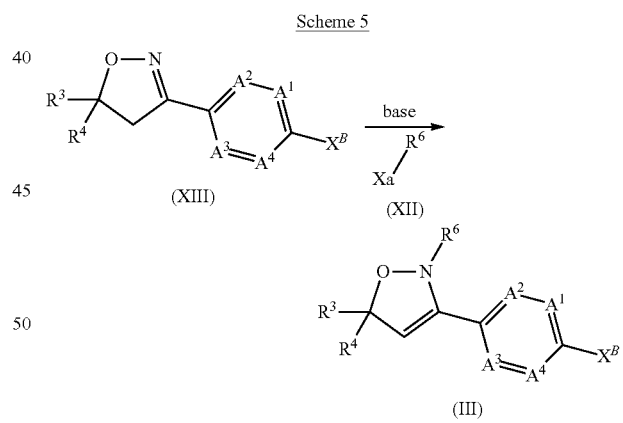

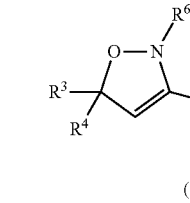

(III)

4) Compounds of formula (III), wherein $R^6$ is other than hydrogen, can be made by treatment of a compound of formula (XIII) with base, such as lithium diisopropylamine ("LDA"), followed by the addition of a compound (XII) wherein $X_a$ is a leaving group, for example an alkylating or an acylating agent, in the presence of a suitable solvent, such as tetrahydrofuran. Suitable alkylating agents are, for example, alkyl halides, such as methyl iodide (Me-I), for making a compound (III) where $R^6$ is $C_1$-$C_8$alkyl, in particular allyl, and acylating agents such as methyl chloroformate, ethyl chloroformate for making a compound (III) where $R^6$ is methoxycarbonyl or ethoxycarbonyl. The reaction is carried out at a temperature of from −120° C. to +30° C., preferably from −100° C. to 0° C. Alternatively, compounds of formula (III), wherein $R^6$ is other than hydrogen, can be made by treatment of a compound of formula (XIII) with a strong alkylating agent, such as trimethyloxonium tetrafluoroborate, in a suitable solvent, for instance 1,2-dichloroethane.

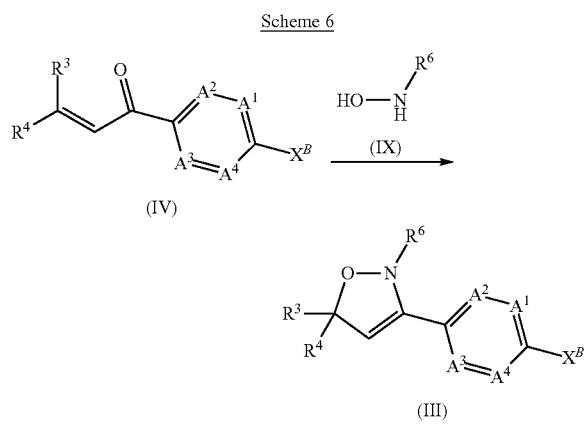

5) Compounds of formula (III), wherein $X^B$ is a leaving group, e.g. a halogen, for instance bromine, can be made by treatment of a compound of formula (IV), wherein $X^B$ is a leaving group, e.g. a halogen, for instance bromine, with a compound of the formula (IX) in a suitable solvent, for instance ethanol. Instead of a compound of the formula (IX), a salt of a compound of the formula (IX), for instance a hydrochloride, can be used for this transformation, in which case the reaction can be carried out in the presence of a base, such as an amine base, for instance triethylamine. The reaction is carried out at a temperature of from −120° C. to +130° C., preferably from −100° C. to 100° C.

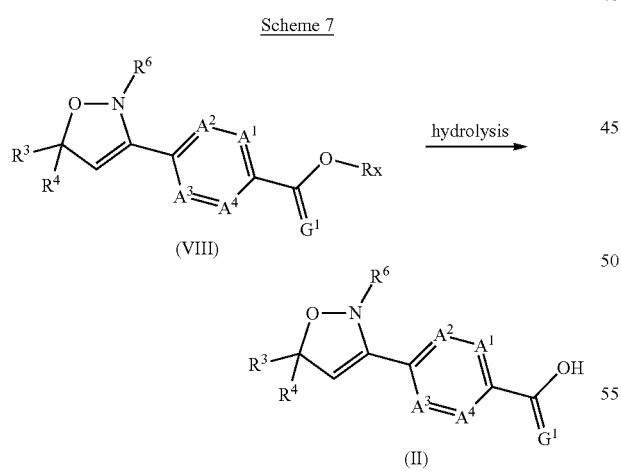

6) Compounds of formula (II), wherein $G^1$ is oxygen, can be made by hydrolysis of a compound of formula (VIII), wherein $G^1$ is oxygen, and $R_x$ is $C_1$-$C_6$alkyl, such as methyl or tert-butyl. For instance, in the case where $R_x$ is methyl or ethyl, the hydrolysis can be done with water and a base, such as potassium hydroxide, in the absence or in the presence of a solvent, such as, for instance, tetrahydrofurane or methynol. In the case where $R_x$ is, for example, tert-butyl, the hydrolysis is done in the presence of acid, such as trifluoroacetic acid or hydrochloric acid. The reaction is carried out at a temperature of from −120° C. to +130° C., preferably from −100° C. to 100° C.

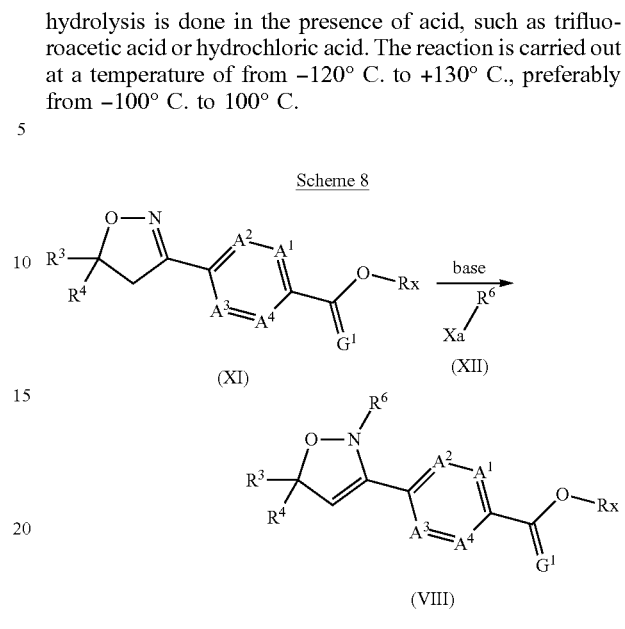

7) Compounds of formula (VIII) wherein $R^6$ is other than hydrogen, wherein $G^1$ is oxygen and $R_x$ is $C_1$-$C_6$alkyl, such as methyl or tert-butyl, can be prepared by reaction of an isoxazoline of formula (XI) wherein $G^1$ is oxygen and $R_x$ is $C_1$-$C_6$alkyl, such as methyl or tert-butyl, with a base and a compound (XII) wherein $X_a$ is a leaving group, for example an alkylating or an acylating agent, in the presence of a suitable solvent, such as tetrahydrofuran. Suitable alkylating agents are, for example, alkyl halides, such as methyl iodide (Me-I), for making a compound (VIII) where $R^6$ is $C_1$-$C_8$alkyl, in particular allyl, and acylating agents such as methyl chloroformate, ethyl chloroformate for making a compound (VIII) where $R^6$ is methoxycarbonyl or ethoxycarbonyl. The reaction is carried out at a temperature of from −120° C. to +30° C., preferably from −100° C. to 0° C.

Scheme 9

8) Compounds of formula (VIII) can be made by treatment of a compound of formula (XVII) with a compound of the formula (IX) in a suitable solvent, for instance ethanol. Instead of a compound of the formula (IX), a salt of a compound of the formula (IX), for instance a hydrochloride, can be used for this transformation, in which case the reaction can be carried out in the presence of a base, such as an amine base, for instance triethylamine. The reaction is carried out at a temperature of from −120° C. to +130° C., preferably from −100° C. to 100° C.

Scheme 10

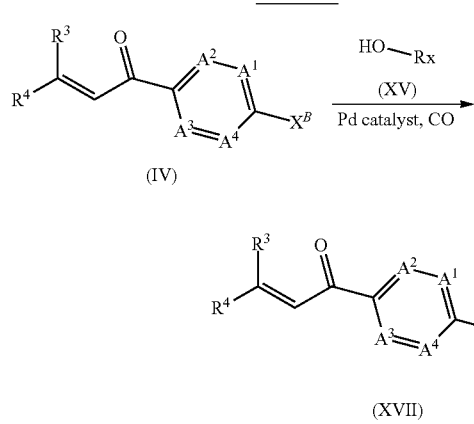

(IV)

(XVII)

9) Compounds of formula (XVII), wherein $G^1$ is oxygen and $R_x$ is $C_1$-$C_6$alkyl, such as, for example, ethyl, can be made by treatment of a compound of formula (IV), wherein $X^B$ is a leaving group, e.g. a halogen, for instance bromine, with a catalyst, such as a palladium catalyst, for instance $PdCl_2(PPh_3)_2$, and a compound of the formula (XV), wherein $R_x$ is $C_1$-$C_6$alkyl, such as, for example, ethyl. Optionally, the reaction is carried out in the presence of a base, such as, for example, triethylamine. The reaction is carried out under an atmosphere of carbon monoxide, at a pressure of 1 to 200 bar, preferably at 10 to 100 bar. The reaction is carried out at a temperature of from −20° C. to +230° C., preferably from 0° C. to 200° C.

Scheme 11

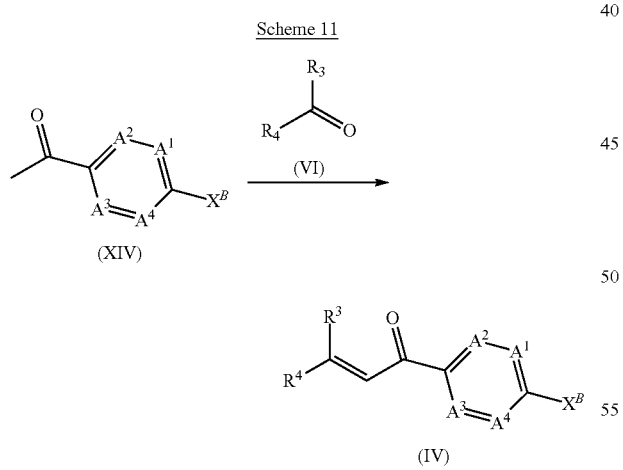

(XIV)

(IV)

10) Compounds of formula (IV) can be made by treatment of a compound of formula (XIV) with a compound of the formula (VI) in a suitable solvent, for instance N,N-dimethylformamide or dichloromethane, in the presence of a base, such as, for example, calcium hydroxide, potassium carbonate or triethylamine. The reaction is carried out at a temperature of from −120° C. to +130° C., preferably from −100° C. to 100° C.

Scheme 12

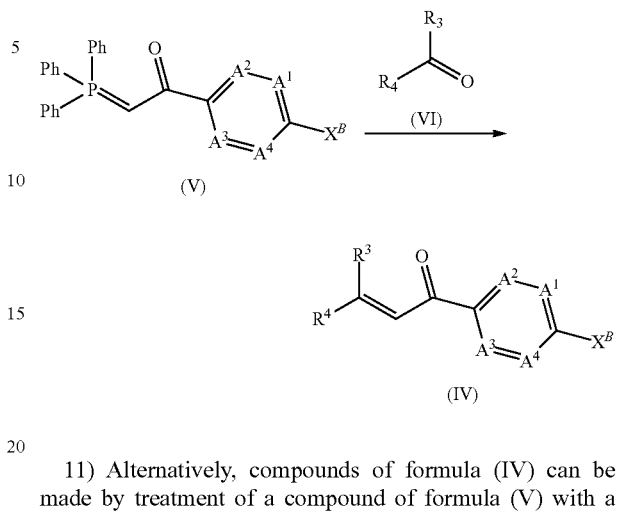

(V)

(IV)

11) Alternatively, compounds of formula (IV) can be made by treatment of a compound of formula (V) with a compound of the formula (VI) in a suitable solvent, for instance toluene. The reaction is carried out at a temperature of from −120° C. to +230° C., preferably from 0° C. to 150° C.

Scheme 13

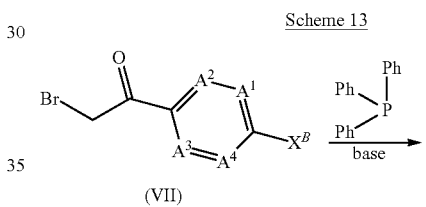

(VII)

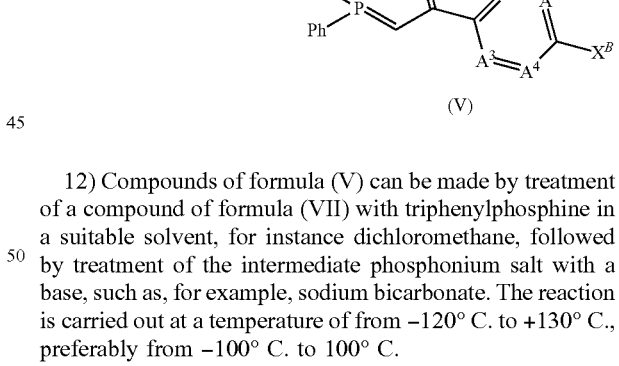

(V)

12) Compounds of formula (V) can be made by treatment of a compound of formula (VII) with triphenylphosphine in a suitable solvent, for instance dichloromethane, followed by treatment of the intermediate phosphonium salt with a base, such as, for example, sodium bicarbonate. The reaction is carried out at a temperature of from −120° C. to +130° C., preferably from −100° C. to 100° C.

Scheme 14

(XVIII) (XIX)

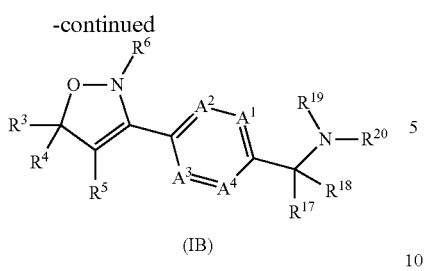

(IB)

13) Compounds of formula (IB), wherein P is P2, $R^{19}$ is as defined above and $R^{20}$ is different from H, can be made by treatment of compounds (XVIII) with a compound (XIX), wherein $X_a$ is a leaving group, for example an acylating agent, in the presence of a suitable solvent, such as tetrahydrofuran, optionally in the presence of a base, such as triethylamine. Suitable acylating agents are, for example, carboxylic acid chlorides such as acetyl chloride, for making a compound (I) where $R^{20}$ is acetyl. Further acylating agents are, for example, carboxylic acid anhydrides, or carboxylic acids in the presence of coupling reagents, which are known to the persons skilled in the art. The reaction is carried out at a temperature of from −120° C. to +130° C., preferably from −50° C. to 50° C.

Scheme 15

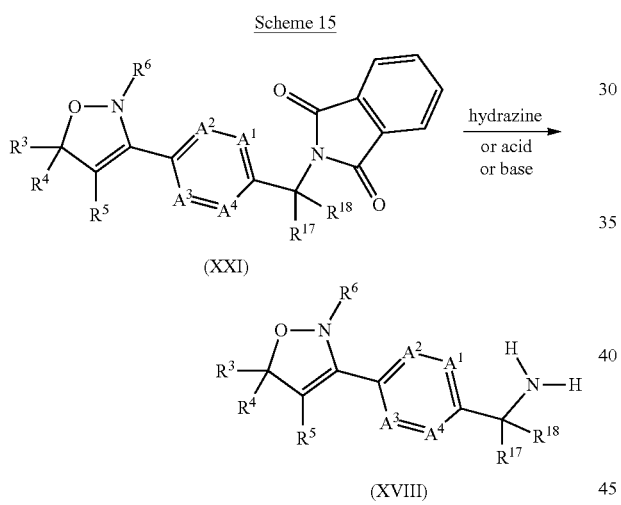

14) Compounds of the formula (XVIII), wherein P is P2 and $R^{19}$ and $R^{20}$ are hydrogen, can be made, for example, by treatment of compounds of the formula (XX) with hydrazine, or with acid, or with base. The reaction is carried out at a temperature of from −120° C. to +130° C., preferably from 0° C. to 100° C.

Scheme 16

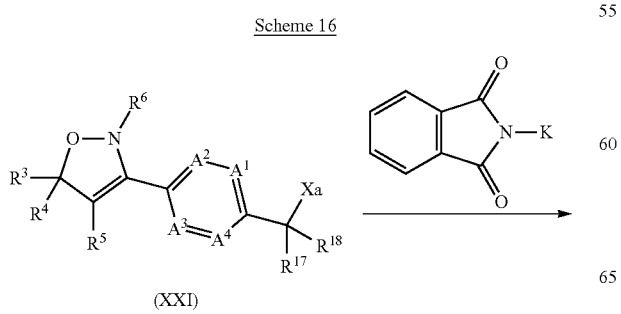

(XXI)

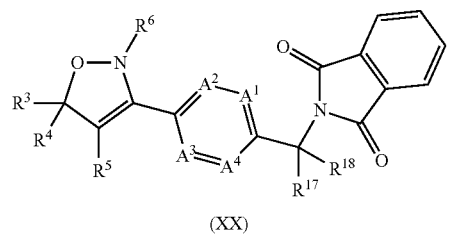

(XX)

15) Compounds of the formula (XX) can be made, for example, by treatment of compounds of the formula (XXI) with potassium phthalimide, or with phthalimide and a suitable base. In formula (XXI), $X_a$ is a leaving group, a halogen for example, such as chlorine. The reaction is carried out at a temperature of from −120° C. to +130° C., preferably from −50° C. to 50° C.

Scheme 17

(XXII)

(XXI)

16) Compounds of the formula (XXI) can be prepared, for example, when Xa is $C_1$, by treatment of compounds (XXII) with thionyl chloride, or, in the case when Xa is Br, by treatment of compounds (XXII) with $PBr_3$ or with triphenylphophine and $CBr_4$. Further such transformations are known to the person skilled in the art. The reaction is carried out at a temperature of from −120° C. to +130° C., preferably from −0° C. to 100° C.

Scheme 18

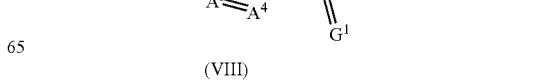

(VIII)

-continued

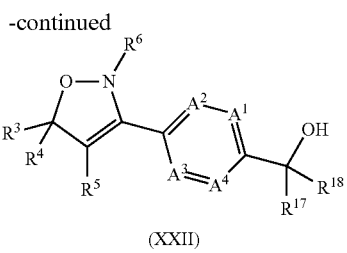

(XXII)

17) Compounds of the formula (XXII), wherein $R^{17}$ and $R^{81}$ are H, can be prepared, for example, by treatment of compounds of formula (VIII), wherein $G^1$ is oxygen and $R_x$ is $C_1$-$C_6$alkyl, such as, for example, ethyl, with a reducing agent, such as, for example, sodium borohydride. The reaction is carried out at a temperature of from −120° C. to +130° C., preferably from −0° C. to 100° C.

Scheme 19

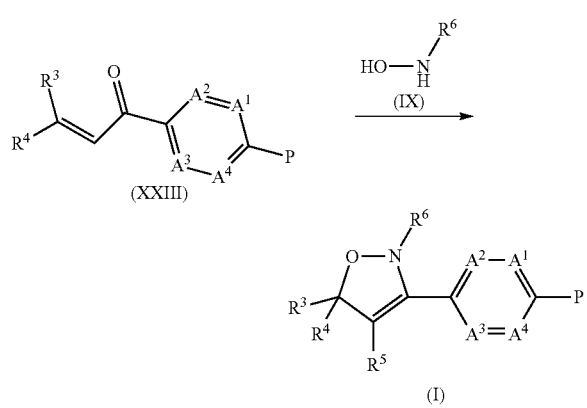

18) Compounds of formula (I), wherein P is P1, P2 or an optionally substituted heterocycle, can be made by treatment of a compound of formula (XXIII) with a compound of the formula (IX) in a suitable solvent, for instance ethanol. Instead of a compound of the formula (IX), a salt of a compound of the formula (IX), for instance a hydrochloride, can be used for this transformation, in which case the reaction can be carried out in the presence of a base, such as an amine base, for instance triethylamine. The reaction is carried out at a temperature of from −120° C. to +130° C., preferably from −100° C. to 100° C.

Scheme 20

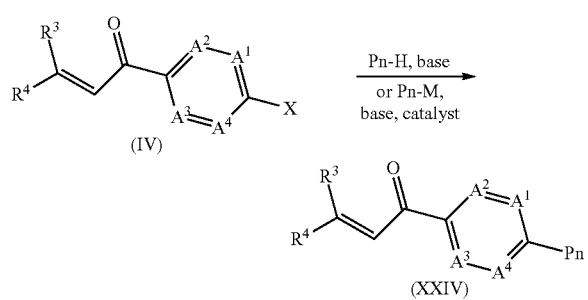

19) Compounds of formula (XXIV), wherein Pn is an optionally substituted heterocycle, can be made, for example in the case where the heterocycle is attached via a nitrogen atom, by treatment of a compound (IV) wherein X is a halogen, such as fluorine, with a heterocyclic compound Pn-H and a suitable base, such as potassium carbonate. Alternatively, compounds of formula (XXIV), wherein Pn is an optionally substituted heterocycle, can be made, for example in the case where the heterocycle is attached via a carbon atom, by treatment of a compound (IV) wherein X is a halogen, such as bromine, with a heterocyclic compound Pn-M, wherein M is hydrogen or a metal, such as boron, magnesium or zink, in which case M can be optionally substituted, with a base and a suitable catalyst, such as a palladium or a copper catalyst, in the presence of a suitable ligand for the catalyst, such as, for example, a diamine ligand, or a phosphine ligand. Such reactions are carried out at a temperature of from −120° C. to +130° C., preferably from −100° C. to 100° C.

Scheme 21

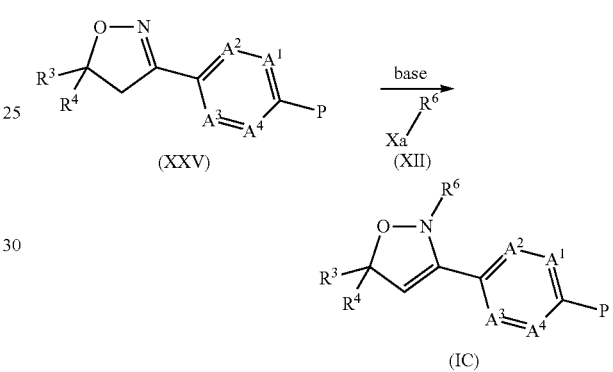

20) Compounds of formula (IC), wherein P is P2 or a heterocycle can be prepared similarly to compounds of formula (IA) in scheme 2.

Compounds of formula (I) contain a chiral centre giving rise to enantiomers of the formula (I*) and (I**).

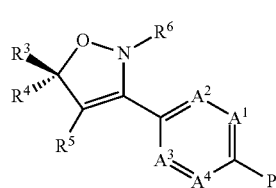

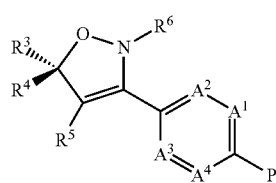

Enantiomerically enriched mixtures of compounds of formula (I*) or (I**) may be prepared, for example, according to schemes 1, 6 or 9 by formation of intermediate III or VIII via an asymmetric cyclization with an N-substituted hydroxylamine. Examples for the cyclization of enones with N-substituted hydroxylamine are described in the literature, such as in Tetrahedron Letters (1975), (34), 2979-80, and references cited therein. Alternatively, such enantiomerically enriched mixtures may be prepared according to schemes 1, 2, 5, 8 or 21 by N-alkylation of enantiomerically enriched mixtures of intermediate XI, XIII, XVI or XXV. N-alkylations of isoxazolines are described, for example, in Farmaco (2005), 60(11-12), 948-954, and references cited therein. Enantiomerically enriched mixtures of intermediates XI, XIII, XVI and XXV can be prepared, for example, in analogy to methods described in the literature, such as, for example, in WO 2009/063910 A1, and references cited therein.

The compounds of formula (I) can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps*(leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalidesfelis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*(vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from Ig to 6 kg per hectare, more preferably from Ig to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole or cyantraniliprole;

t) Sulfoxaflor;

u) Metaflumizone;

v) Fipronil and Ethiprole;

w) Pyrifluqinazon x) buprofezin; or y) 4-[(6-Chloro-pyridin-3-ylmethyl)-(2,2-difluoro-ethyl)-amino]-5H-furan-2-one (DE 102006015467).

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)—N-methyl-2-[2-(2,5-dimethylphenoxymethyl) phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)—N-benzyl-N- ([methyl (methyl-thioethylideneamino-oxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-iso-propyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-A1, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb, ziram; 1,3-Dimethyl-1H-pyrazole-4-carboxylic acid (4'-methylsulfanyl-biphenyl-2-yl)-amide, 1,3-Dimethyl-1H-pyrazole-4-carboxylic acid (2-dichloromethylene-3-ethyl-1-methyl-indan-4-yl)-amide, and 1,3-Dimethyl-4H-pyrazole-4-carboxylic acid [2-(2,4-dichloro-phenyl)-2-methoxy-1-methyl-ethyl]-amide. The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epspirantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neoasozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms. Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the compounds of the invention allows more economic and simple husbandry of animals.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as Nematodirus, *Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy* hides, *Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, ($6^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalidesfelis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites including: flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly adminstration intervals (i.e. administering the compounds to the animal once every month).

The following Examples illustrate, but do not limit, the invention.

PREPARATION EXAMPLES

Example I1: 1-(4-Bromo-3-methyl-phenyl)-2-(triphenylphosphanylidene)-ethanone (Va)

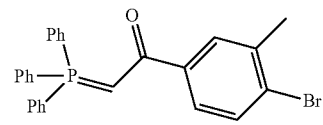 [SMILES: Cc1cc(C(=O)C=P(c2ccccc2)(c2ccccc2)c2ccccc2)ccc1Br]

1300 mg of 2-Bromo-1-(4-bromo-3-methyl-phenyl)-ethanone (VIIa) (Journal of Organic Chemistry (1947), 12, 617-703) was stirred with 1300 mg of triphenylphosphine in 20 ml of dichloromethane at ambient temperature for 18 hours. The mixture was diluted with toluene and the separated phosphonium salt was filtered off. It was then suspended in 20 ml of dichloromethane and 20 ml of water. 800 mg (7.55 mmol) of sodium bicarbonate was then added in 20 ml of water and the mixture was stirred overnight. The organic layer was separated, dried and evaporated under reduced pressure. The residue was triturated with hexane giving 1.6 g (86%) of 1-(4-Bromo-3-methyl-phenyl)-2-(triphenylphosphanylidene)-ethanone (Va) as a solid. $^1$H-NMR (CDCl$_3$, δ in ppm): 7.40-7.90 (m, 18H), 4.40 (m, 1H).

Example I2: 1-(4-Bromo-3-methyl-phenyl)-3-(3,5-dichloro-phenyl)-4,4,4-trifluoro-but-2-en-1-one (IVa)

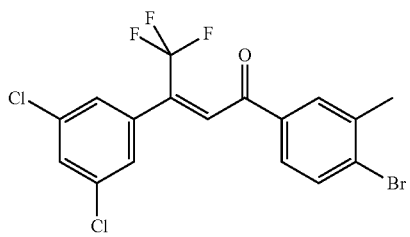 [SMILES: Cc1cc(C(=O)/C=C(/c2cc(Cl)cc(Cl)c2)C(F)(F)F)ccc1Br]

473 mg of 1-(4-Bromo-3-methyl-phenyl)-2-(triphenyl-phosphanylidene)-ethanone (Va) was refluxed with 243 mg of 1-(3,5-Dichloro-phenyl)-2,2,2-trifluoro-ethanone (VIa) (Journal of Physical Organic Chemistry (1989), 2(4), 363-6) in 3 ml of toluene for 3 hours. The solvent was then evaporated, and the residue was triturated with the mixture hexane:ethyl acetate 20:1. The solid that separated was filtered off and the filtrate after evaporation was purified on silica gel (40 g, hexane:acetate 10:1) giving 380 mg (86%) of 1-(4-Bromo-3-methyl-phenyl)-3-(3,5-dichloro-phenyl)-4,4,4-trifluoro-but-2-en-1-one (IVa) as a yellow oil which solidified on standing (mixture of E and Z isomers). $^1$H-NMR (CDCl$_3$, δ in ppm): 2.41 (s) and 2.46 (s) (total of 3H), 6.80-7.80 (m, total of 7H).

Example I3: 3-(4-Bromo-3-methyl-phenyl)-5-(3,5-dichloro-phenyl)-2-methyl-5-trifluoromethyl-2,5-dihydro-isoxazole (IIIa)

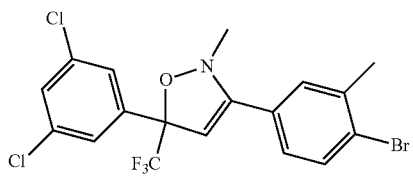 [SMILES: Cc1cc(C2=CC(c3cc(Cl)cc(Cl)c3)(C(F)(F)F)ON2C)ccc1Br]

300 mg 1-(4-Bromo-3-methyl-phenyl)-3-(3,5-dichloro-phenyl)-4,4,4-trifluoro-but-2-en-1-one (IVa), 80 mg MeNHOH.HCl and 100 mg triethylamine were refluxed in 2 ml of ethanol for 18 hours. After evaporation of the solvent the residue was purified on silica gel giving 210 mg (65%) of 3-(4-Bromo-3-methyl-phenyl)-5-(3,5-dichloro-phenyl)-2-methyl-5-trifluoromethyl-2,5-dihydro-isoxazole (IIIa) as a colorless resin.

7.56 (d, 1H), 7.44 (s, 2H), 7.36 (t, 1H), 7.33 (d, 1H), 7.13 (dd, 1H), 5.35 (s, 1H), 2.95 (s, 3H), 2.40 (s, 3H).

Example I4: 4-[5-(3,5-Dichloro-phenyl)-2-methyl-5-trifluoromethyl-2,5-dihydro-isoxazol-3-yl]-2-methyl-benzoic Acid (IIa)

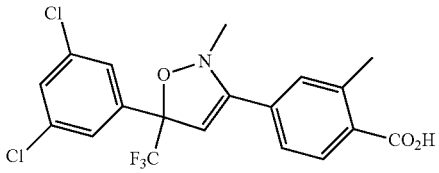 [SMILES: Cc1cc(C2=CC(c3cc(Cl)cc(Cl)c3)(C(F)(F)F)ON2C)ccc1C(=O)O]

210 mg of 3-(4-Bromo-3-methyl-phenyl)-5-(3,5-dichloro-phenyl)-2-methyl-5-trifluoromethyl-2,5-dihydro-isoxazole (IIIa) was dissolved in 20 ml of dry THF, cooled to −90° C. and treated with 0.625 ml BuLi 1.6M in hexane. The mixture was stirred for 1 hour at −80° C. and then a great excess of solid CO$_2$ was added to the mixture. The temperature was allowed to rise up to −30° C. (1 hour) and 5 ml of 1M HCl was added followed with ether. The organic layer was dried and evaporated to dryness. The residual resin was used in the final step without purification.

Example P1 (Compound A3 from Table A): N-Butyl-4-[5-(3,5-dichloro-phenyl)-2-methyl-5-trifluoromethyl-2,5-dihydro-isoxazol-3-yl]-2-methyl-benzamide

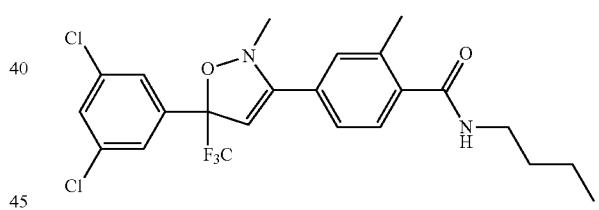

200 mg of 4-[5-(3,5-Dichloro-phenyl)-2-methyl-5-trifluoromethyl-2,5-dihydro-isoxazol-3-yl]-2-methyl-benzoic acid (IIa), 127 mg of oxalylchloride and one drop of DMF were stirred in 10 ml of dichloromethane overnight. The volatiles were evaporated under reduced pressure, the residue was dissolved in 5 ml of dichloromethane and then treated with 150 mg of n-butylamine. The mixture was stirred at ambient temperature for 3 hours, washed with diluted HCl and after evaporation the residue was purified on silica gel giving 65 mg of N-Butyl-4-[5-(3,5-dichloro-phenyl)-2-methyl-5-trifluoromethyl-2,5-dihydro-isoxazol-3-yl]-2-methyl-benzamide (Ia) as a colorless resin. $^1$H-NMR (CDCl$_3$, δ in ppm): 7.23-7.51 (m, 6H), 5.70 (t, 1H), 5.31 (s, 1H), 3.49 (q, 2H), 2.98 (s, 3H), 2.37 (s, 3H), 1.61 (m, 2H), 1.45 (m, 2H), 0.96 (t, 3H).

Example I5: 4-[3-(3,5-Dichloro-phenyl)-4,4,4-trifluoro-but-2-enoyl]-2-methyl-benzoic Acid ethyl ester (XVIIa)

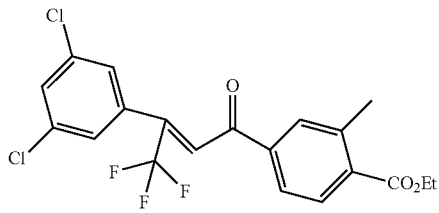 [SMILES: CCOC(=O)c1ccc(C(=O)/C=C(/c2cc(Cl)cc(Cl)c2)C(F)(F)F)cc1C]

To a solution of 1 g 1-(4-Bromo-3-methyl-phenyl)-3-(3,5-dichloro-phenyl)-4,4,4-trifluoro-but-2-en-1-one (IVa) in 40 ml of absolute ethanol was added 1 ml of triethylamine and 150 mg of PdCl$_2$(PPh$_3$)$_2$. The mixture was then heated in an autoclave under 60 bar of CO at 120° C. for 20 hours. Concentration of the mixture followed by column chromatography (silica gel) afforded 0.66 g (67%) of 4-[3-(3,5-Dichloro-phenyl)-4,4,4-trifluoro-but-2-enoyl]-2-methyl-benzoic acid ethyl ester (IXa) as an oil, which crystallized on standing. $^1$H-NMR (CDCl$_3$, δ in ppm): 7.93 (q, 1H), 7.66 (m, 2H), 7.15-7.39 (m, 4H), 4.38 (q, 2H), 2.62 (s, 3H), 1.40 (t, 3H).

Example I6: 4-[5-(3,5-Dichloro-phenyl)-2-methyl-5-trifluoromethyl-2,5-dihydro-isoxazol-3-yl]-2-methyl-benzoic Acid ethyl ester (VIIIa)

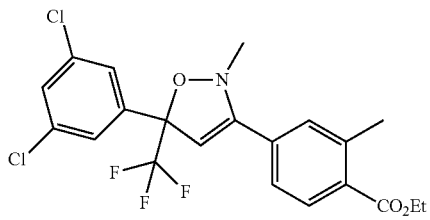 [SMILES: CCOC(=O)c1ccc(C2=CC(c3cc(Cl)cc(Cl)c3)(C(F)(F)F)ON2C)cc1C]

0.62 g of 4-[3-(3,5-Dichloro-phenyl)-4,4,4-trifluoro-but-2-enoyl]-2-methyl-benzoic acid ethyl ester (XVIIa) was mixed with 0.21 g of N-methylhydroxylamine hydrochloride and 0.42 ml of triethylamine in 10 ml of dry ethanol. The mixture was refluxed for 20 hours, evaporated to dryness and purified on silica gel giving 0.275 g (42%) of 4-[5-(3,5-Dichloro-phenyl)-2-methyl-5-trifluoromethyl-2,5-dihydro-isoxazol-3-yl]-2-methyl-benzoic acid ethyl ester (VIIIa) as a colorless oil. $^1$H-NMR (CDCl$_3$, δ in ppm): 7.93 (d, 1H), 7.30-7.45 (m, 5H), 5.43 (s, 1H), 4.37 (q, 2H), 2.99 (s, 3H), 2.61 (s, 3H), 1.40 (t, 3H).

Example I7: 4-[5-(3,5-Dichloro-phenyl)-2-methyl-5-trifluoromethyl-2,5-dihydro-isoxazol-3-yl]-2-methyl-benzoic Acid (IIa)

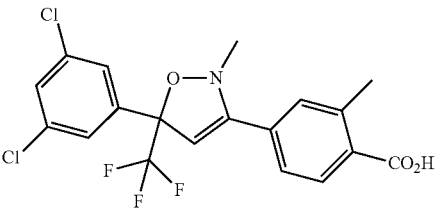 [SMILES: Cc1cc(C2=CC(c3cc(Cl)cc(Cl)c3)(C(F)(F)F)ON2C)ccc1C(=O)O]

0.27 g of 4-[5-(3,5-Dichloro-phenyl)-2-methyl-5-trifluoromethyl-2,5-dihydro-isoxazol-3-yl]-2-methyl-benzoic acid ethyl ester (VIIIa) was stirred in a mixture of 5 ml of methanol, 5 ml of THF and 1 ml of water. To this solution 0.2 g KOH was added and the mixture was stirred for 5 days at ambient temperature. The solvents were then evaporated, the residue was diluted with water and acidified with 1N HCl. The solid that precipitated was isolated by filtration and dried to give 0.240 g (95%) of 4-[5-(3,5-Dichloro-phenyl)-2-methyl-5-trifluoromethyl-2,5-dihydro-isoxazol-3-yl]-2-methyl-benzoic acid (IIa) as a pale solid. $^1$H-NMR (CDCl$_3$, δ in ppm): 8.05 (d, 1H), 7.26-7.44 (m, 5H), 5.46 (s, 1H), 3.00 (s, 3H), 2.65 (s, 3H).

Example I8: Preparation of 4-[5-(3,5-Dichloro-phenyl)-2,5-dimethyl-2,5-dihydro-isoxazol-3-yl]-2-methyl-benzamide

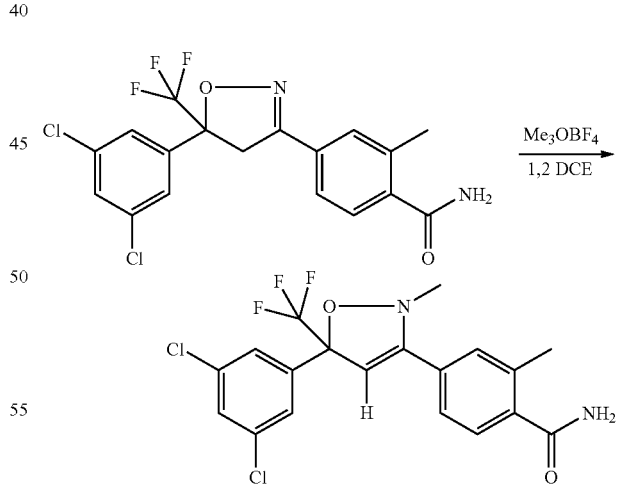

To a solution of 4-[5-(3,5-Dichloro-phenyl)-5-trifluoromethyl-4,5-dihydro-isoxazol-3-yl]-2-methyl-benzamide (200 mg) in 1,2-dichloroethane (3 ml) was added trimethyloxonium tetrafluoroborate (85 mg) and the reaction mixture was stirred at room temperature for 19 hours then more trimethyloxonium tetrafluoroborate (210 mg). After 4 hours 30 minutes, more trimethyloxonium tetrafluoroborate (0.5 ml) was added and after 2 hours, the reaction mixture was heated at (85° C.) for 18 hours. The solution was then concentrated under vacuo to give a crude residue (210 mg). Part of this residue (100 mg) of the crude was extracted between AcOEt and saturated NaHCO$_3$. The organic phases were gathered, dried over anhydrous MgSO$_4$, filtered and evaporated to give the desired compound (54 mg). $^1$H-NMR (CDCl$_3$, δ in ppm): 7.50-7.31 (m, 6H), 5.75 (bs, 2H), 5.41 (s, 1H), 2.99 (s, 3H), 2.52 (s, 3H). The preparation of 4-[5-(3,5-Dichloro-phenyl)-5-trifluoromethyl-4,5-dihydro-isoxazol-3-yl]-2-methyl-benzamide is disclosed in WO 2005/085216.

Example I9: Preparation of 3-(4-tert-Butoxycarbonyl-3-methyl-phenyl)-5-(3,5-dichloro-phenyl)-5-methyl-5H-isoxazole-2-carboxylic Acid methyl ester

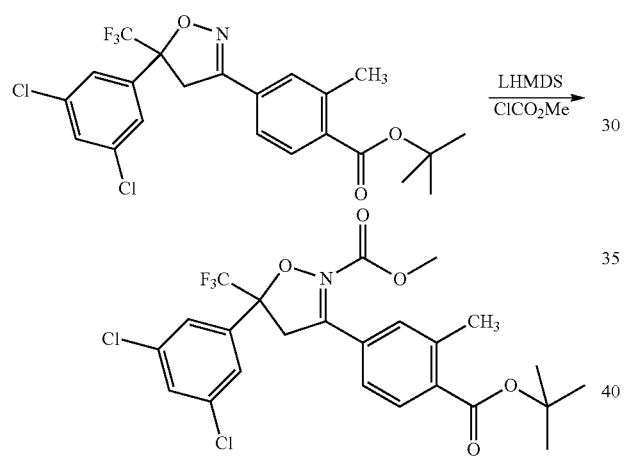

To a solution of 4-[5-(3,5-Dichloro-phenyl)-5-methyl-4,5-dihydro-isoxazol-3-yl]-2-methyl-benzoic acid tert-butyl ester (1.3 g) in dry tetrahydrofuran (15 ml) stirred under argon at −78° C., was added lithium hexamethyldisilazane ("LHMDS") (1 M in hexane) (3.45 ml). The solution was stirred at −78° C. until deprotonation was completed as monitored by thin layer chromatography. Then, to this solution was added methyl chloroformate (0.465 ml) and the reaction mixture was stirred at −78° C. for 2 hours. The mixture was quenched with saturated ammonium chloride and then extracted with ethyl acetate. The combined organic extracts were dried over magnesium sulfate and concentrated. The residue was purified by chromatography on silica gel (eluent: heptane/diisopropylether 1:1) to give 3-(4-tert-butoxycarbonyl-3-methyl-phenyl)-5-(3,5-dichloro-phenyl)-5-methyl-5H-isoxazole-2-carboxylic acid methyl ester (472 mg) as a yellow foam.

$^1$H-NMR (CDCl$_3$, 400 MHz): 7.84 (d, 1H, J=8.44 Hz), 7.50 (m, 2H), 7.43 (m, 1H), 7.35 (m, 2H), 5.70 (s, 1H), 3.81 (s, 3H), 2.59 (s, 3H), 1.60 (s, 9H) ppm.

Similarly, 3-(4-tert-Butoxycarbonyl-3-methyl-phenyl)-5-(3,5-dichloro-phenyl)-5-me thyl-5H-isoxazole-2-carboxylic acid ethyl ester was obtained using ethylchloroformate as an electrophile. $^1$H-NMR (CDCl$_3$, 400 MHz): 7.84 (d, 1H, J=8.80 Hz), 7.51 (m, 2H), 7.43 (m, 1H), 7.37 (m, 2H), 5.71 (s, 1H), 4.24 (q, 2H, J=6.97 Hz), 2.59 (s, 3H), 1.60 (s, 9H), 1.28 (t, 3H, J=6.97 Hz), ppm.

4-[5-(3,5-Dichloro-phenyl)-5-methyl-4,5-dihydro-isoxazol-3-yl]-2-methyl-benzoic acid tert-butyl ester is disclosed in WO 2009/080250

Example I10: 5-[3-(3,5-Dichloro-phenyl)-4,4,4-trifluoro-but-2-enoyl]-2-fluoro-benzonitrile

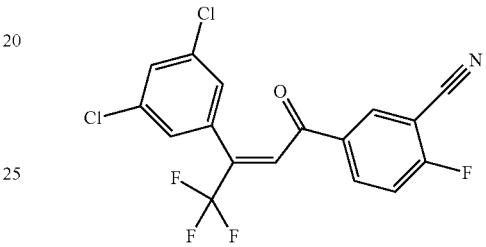

163 mg of 1-(3,5-Dichloro-phenyl)-2,2,2-trifluoro-ethanone (VIa) (Journal of Physical Organic Chemistry (1989), 2(4), 363-6), 486 mg of 5-acetyl-2-fluoro-benzonitrile (CAS:288309-07-9) and 276 mg of potassium carbonate in 5 ml of dry toluene were refluxed for 72 hours. The solvent was then evaporated under reduced pressure and the residue was purified on silica gel (eluent hexane/ethyl acetate 6:1) affording 5-[3-(3,5-Dichloro-phenyl)-4,4,4-trifluoro-but-2-enoyl]-2-fluoro-benzonitrile as a yellow resin in 46% yield (solidified on standing). $^1$H-NMR (CDCl$_3$, δ in ppm): 8.05-8.11 (m, 2H), 7.33-7.43 (m, 3H), 7.15 (s, 2H).

Example I11: 5-[3-(3,5-Dichloro-phenyl)-4,4,4-trifluoro-but-2-enoyl]-2-[1,2,4]triazol-1-yl-benzonitrile

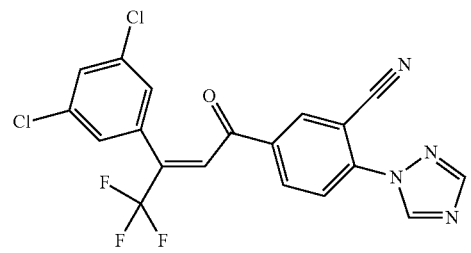 [SMILES: N#Cc1cc(C(=O)/C=C(\c2cc(Cl)cc(Cl)c2)C(F)(F)F)ccc1-n1cncn1]

310 mg of 5-[3-(3,5-Dichloro-phenyl)-4,4,4-trifluoro-but-2-enoyl]-2-fluoro-benzonitrile (Example I10) 73 mg of 1,2,4-triazole and 166 mg of potassium carbonate were stirred in 5 ml acetonitrile at room temperature for 24 hours. The solid was filtered off and the filtrate was evaporated under reduced pressure. The residue was purified on silica gel (elutant diethylether) affording 5-[3-(3,5-dichloro-phenyl)-4,4,4-trifluoro-but-2-enoyl]-2-[1,2,4]triazol-1-yl-benzonitrile as a solid in 71% yield. $^1$H-NMR (CDCl$_3$, δ in ppm): 8.96 (s, 1H), 8.17-8.28 (m, 3H), 7.99 (d, 1H), 7.37-7.39 (m, 2H), 7.17 (s, 2H).

Example P2: 5-[5-(3,5-Dichloro-phenyl)-2-methyl-5-trifluoromethyl-2,5-dihydro-isoxazol-3-yl]-2-[1,2,4]triazol-1-yl-benzonitrile (Compound No. C1)

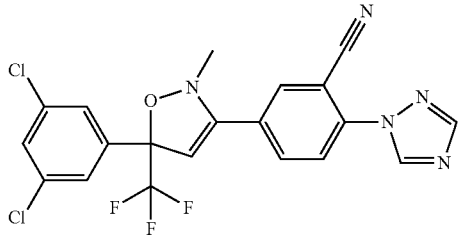 [SMILES: CN1OC(c2cc(Cl)cc(Cl)c2)(C(F)(F)F)C=C1c1ccc(-n2cncn2)c(C#N)c1]

437 mg of 5-[3-(3,5-Dichloro-phenyl)-4,4,4-trifluoro-but-2-enoyl]-2-[1,2,4]triazol-1-yl-benzonitrile (Example I11), 85 mg of N-methylhydroxylamine hydrochloride and 103 mg triethylamine were dissolved in 25 ml ethanol and refluxed for 72 hours. Evaporation of the solvent and purification on silica gel (eluent hexane/ethyl acetate 1:1) afforded 200 mg of a mixture of the product and the starting enone. The mixture was treated with an excess of methylhydroxylamine hydrochloride (200 mg) and TEA (300 mg) in refluxing ethanol for 30 min. Evaporation of the solvent and purification on silica gel (hexane/ethyl acetate 2:1) afforded 5-[5-(3,5-dichloro-phenyl)-2-methyl-5-trifluoromethyl-2,5-dihydro-isoxazol-3-yl]-2-[1,2,4]triazol-1-yl-benzonitrile (27 mg) as a resin. $^1$H-NMR (CDCl$_3$, δ in ppm): 8.86 (s, 1H), 8.21 (s, 1H), 7.83-7.95 (m, 3H), 7.39-7.45 (m, 3H), 5.55 (s, 1H), 3.02 (s, 3H).

Example I12: {4-[5-(3,5-Dichloro-phenyl)-2-methyl-5-trifluoromethyl-2,5-dihydro-isoxazol-3-yl]-2-methyl-phenyl}-methanol

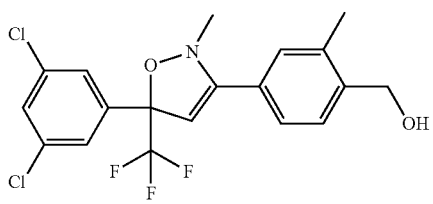 [SMILES: Cc1cc(C2=CC(c3cc(Cl)cc(Cl)c3)(C(F)(F)F)ON2C)ccc1CO]

414 mg of 4-[5-(3,5-Dichloro-phenyl)-2-methyl-5-trifluoromethyl-2,5-dihydro-isoxazol-3-yl]-2-methyl-benzoic acid ethyl ester (VIIIa) and 152 mg of sodium borohydride were suspended in 10 ml tetrahydrofurane. The mixture was heated to 60° C. and 0.85 ml of methanol was the added dropwise under vigorous stirring. The mixture was stirred at 60° C. until the gas evolution subsided. The mixture was then cooled and ice water followed by diethylether were added. Then a solution of hydrochloric acid (1N) was slowly added to acidify the solution. The organic phase was washed with water and dried. Evaporation of the solvent afforded {4-[5-(3,5-Dichloro-phenyl)-2-methyl-5-trifluoromethyl-2,5-dihydro-isoxazol-3-yl]-2-methyl-phenyl}-methanol as a solidified foam in 98% yield. $^1$H-NMR (CDCl$_3$, δ in ppm): 7.28-7.45 (m, 6H), 5.34 (s, 1H), 4.72 (s, 2H), 2.99 (s, 3H), 2.35 (s, 3H).

Example I13: 3-(4-Chloromethyl-3-methyl-phenyl)-5-(3,5-dichloro-phenyl)-2-methyl-5-trifluoromethyl-2,5-dihydro-isoxazole

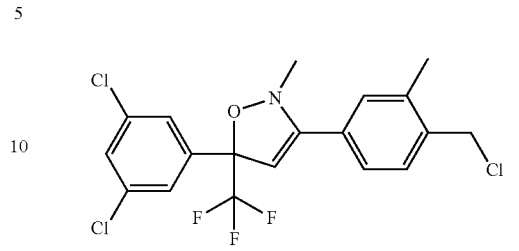

690 mg of {4-[5-(3,5-Dichloro-phenyl)-2-methyl-5-trifluoromethyl-2,5-dihydro-isoxazol-3-yl]-2-methyl-phenyl}-methanol was dissolved in 20 ml dichloromethane and one drop of N,N-dimethylformamide was then added. Thionylchloride (216 mg) was then added very slowly at room temperature. The mixture turned slight yellow before the end of the addition. The mixture was stirred for 3 hours at ambient temperature and then evaporated to dryness. The residue was dissolved in diethylether, washed with aqueous sodium bicarbonate, then with water and finally dried over anhydrous sodium sulfate. The organic phase was then evaporated to dryness affording 3-(4-chloromethyl-3-methyl-phenyl)-5-(3,5-dichloro-phenyl)-2-methyl-5-trifluoromethyl-2,5-dihydro-isoxazole as a resinous product (99% yield), which was used immediately for the further step without purification. $^1$H-NMR (CDCl$_3$, δ in ppm): 7.29-7.44 (m, 6H), 5.36 (s, 1H), 4.60 (s, 2H), 2.99 (s, 3H), 2.44 (s, 3H).

Example I14: 2-{4-[5-(3,5-Dichloro-phenyl)-2-methyl-5-trifluoromethyl-2,5-dihydro-isoxazol-3-yl]-2-methyl-benzyl}-isoindole-1,3-dione

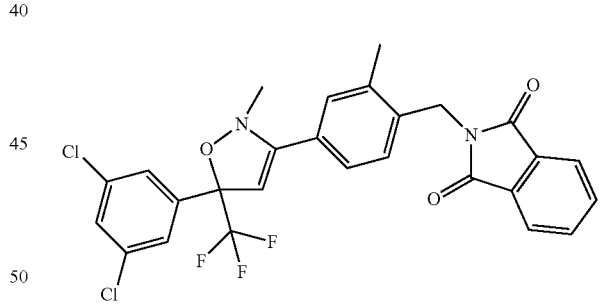

524 mg of 3-(4-Chloromethyl-3-methyl-phenyl)-5-(3,5-dichloro-phenyl)-2-methyl-5-trifluoromethyl-2,5-dihydro-isoxazole, 216 mg of potassium phthalimide and 10 mg sodium iodide in 7 ml N,N-dimethylformamide were stirred at ambient temperature overnight. The mixture was diluted with water (100 ml) and extracted with 200 ml of ether. The organic phase was washed with water and dried. Evaporation of the solvent afforded a foam. Trituration with hexane gave 2-{4-[5-(3,5-Dichloro-phenyl)-2-methyl-5-trifluoromethyl-2,5-dihydro-isoxazol-3-yl]-2-methyl-benzyl}-isoindole-1,3-dione as a white solid in 98% yield.

$^1$H-NMR (CDCl$_3$, δ in ppm): 7.88 (m, 2H), 7.75 (m, 2H), 7.22-7.43 (m, 6H), 5.30 (s, 1H), 4.86 (s, 2H), 2.96 (s, 3H), 2.50 (s, 3H).

Example I15: 4-[5-(3,5-Dichloro-phenyl)-2-methyl-5-trifluoromethyl-2,5-dihydro-isoxazol-3-yl]-2-methyl-benzylamine

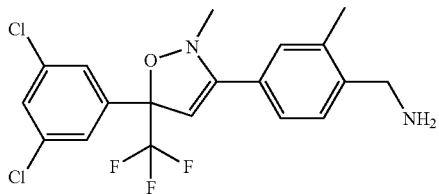 [SMILES: Cc1cc(C2=CC(c3cc(Cl)cc(Cl)c3)(C(F)(F)F)ON2C)ccc1CN]

837 mg of 2-{4-[5-(3,5-Dichloro-phenyl)-2-methyl-5-trifluoromethyl-2,5-dihydro-isoxazol-3-yl]-2-methyl-benzyl}-isoindole-1,3-dione (Example 114) and 500 mg hydrazine hydrate in 25 ml ethanol were heated at reflux for 2 hours under stirring. The mixture was cooled and diluted with diethyl ether. The solid was filtered off and the filtrate was evaporated. The residue was dissolved in 100 ml of ether and washed with water. The organic phase was dried and evaporated. The residue was purified on silica gel (eluent dichloromethane/methanol 4:1) affording 4-[5-(3,5-dichloro-phenyl)-2-methyl-5-trifluoromethyl-2,5-dihydro-isoxazol-3-yl]-2-methyl-benzylamine as a resin in 65% yield. $^1$H-NMR (CDCl$_3$, δ in ppm): 7.44 (s, 2H), 7.37 (m, 2H), 7.28 (m, 2H), 5.33 (s, 1H), 3.88 (s, 2H), 2.99 (s, 3H), 2.34 (s, 3H).

The compounds of Table A were prepared in a similar manner as described in Example P1.

The compounds of Table B were prepared from 4-[5-(3,5-Dichloro-phenyl)-2-methyl-5-trifluoromethyl-2,5-dihydro-isoxazol-3-yl]-2-methyl-benzylamine (Example 115) by methods known per se.

The following abbreviations were used throughout this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; RT=retention time; MH$^+$=molecular cation.

The following LC-MS method was used to characterize the compounds:

Method A:

| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
|---|---|
| LC | 1100er Series HPLC from Agilent: quaternary pump, heated column compartment and diode-array detector. Column: Waters Atlantis dc18; length: 20 mm; internal diameter: 3 mm; particle size: 3 µm, temperature (° C.) 40, DAD wavelength range (nm): 200 to 500, solvent gradient: A = 0.1% of formic acid in water and B: 0.1% of formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method B:
ACQUITY SQD Mass Spectrometer from Waters (Single quadrupole mass spectrometer) Ionisation method: Electrospray Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

TABLE A

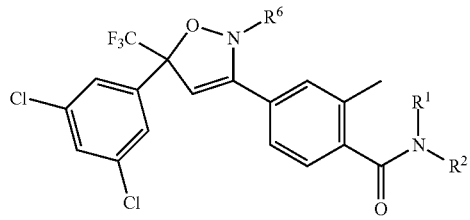

(Ib)

| Comp No. | R$^1$ | R$^2$ | R$^6$ | RT (min) | MH$^+$ | Method |
|---|---|---|---|---|---|---|
| A1 | 2,2,2-Trifluoro-ethyl | H | Me | 4.58 | 513/515/517 | A |
| A2 | Ethyl | H | Me | 4.75 | 459/461/463 | A |
| A3 | n-Butyl | H | Me | 4.7 | 487/489/491 | A |
| A4 | 2-Methoxy-1-methyl-ethyl | H | Me | 4.63 | 503/505/507 | A |
| A5 | (1H-Benzoimidazol-2-yl)-methyl | H | Me | 3.22 | 561/563/565 | A |
| A6 | 3,3,3-Trifluoro-propyl | H | Me | 4.86 | 527/529/531 | A |
| A7 | sec-Butyl | H | Me | 5.18 | 487/489/491 | A |
| A8 | (Tetrahydro-furan-2-yl)-methyl | H | Me | 4.47 | 515/517/519 | A |
| A9 | Benzyl | H | Me | 4.44 | 521/523/525 | A |
| A10 | 2-Fluoro-benzyl | H | Me | 4.24 | 539/541/543 | A |
| A11 | 1-Phenyl-ethyl | H | Me | 4.78 | 535/537/539 | A |
| A12 | 4-Methoxy-benzyl | H | Me | 4.93 | 551/553/555 | A |
| A13 | 1,1-Dioxo-thietan-3-yl | H | Me | 4.91 | 535/537/539 | A |
| A14 | (6-Chloro-pyridin-3-yl)-methyl | H | Me | 5.03 | 556/558/560/562 | A |
| A15 | 3-Fluoro-phenyl | H | Me | 5.07 | 525/527/529 | A |
| A16 | Pyridin-2-yl-methyl | H | Me | 4.6 | 522/524/526 | A |
| A17 | 2,5-Dimethyl-2H-pyrazol-3-yl | H | Me | 4.89 | 525/527/529 | A |
| A18 | 4-Methyl-thiazol-2-yl | H | Me | 5.19 | 528/530/532 | A |
| A19 | 3-Methyl-thietan-3-yl | H | Me | 4.89 | 517/519/521 | A |
| A20 | 1,1-Dimethyl-2-methylsulfanyl-ethyl | H | Me | 5.25 | 533/535/537 | A |
| A21 | 1-Oxo-thietan-3-yl | H | Me | 4.49 | 519/521/523 | A |

TABLE A-continued

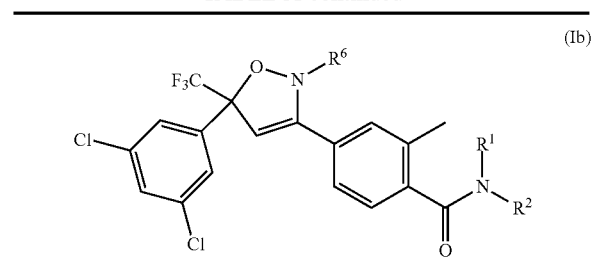

(Ib)

| Comp No. | R¹ | R² | R⁶ | RT (min) | MH⁺ | Method |
|---|---|---|---|---|---|---|
| A22 | Thietan-3-yl | H | Me | 4.88 | 503/505/507 | A |
| A23 | Bicyclo[2.2.1]hept-2-yl | H | Me | 4.99 | 525/527/529 | A |
| A24 | Cyclobutyl | H | Me | 5.02 | 485/487/489 | A |
| A25 | H | H | Me | 2.05 | 429/431/433 | A |
| A26 | Thietan-3-yl | H | Allyl | 2.25 | 527/529/531 | A |
| A27 | (R)-2-ethyl-isoxazolidin-3-one-4-yl | H | Me | 1.96 | 544/546/548 | B |
| A28 | (R)-2-(2,2,2-trifluoro-ethyl)-isoxazolidin-3-one-4-yl | H | Me | 2.05 | 598/600/602 | B |
| A29 | 2-Oxo-[1,2]oxathiolan-4-yl | H | Me | 1.89 | 535/537/539 | B |
| A30 | 2-Oxo-[1,2]oxathiolan-4-yl | H | Me | 1.94 | 535/537/539 | B |
| A31 | 2,2,2-Trifluoro-ethyl | H | benzyl | 2.25 | 589/591/593 | B |
| A32 | Ethyl | H | benzyl | 2.17 | 535/537/539 | B |
| A33 | Butyl | H | benzyl | 2.32 | 563/565/567 | B |
| A34 | 2-Methoxy-1-methyl-ethyl | H | benzyl | 2.21 | 579/581/583 | B |
| A35 | (2,2,2-Trifluoro-ethylcarbamoyl)-methyl | H | benzyl | 2.12 | 646/648/650 | B |
| A36 | 3,3,3-Trifluoro-propyl | H | benzyl | 2.26 | 603/605/607 | B |
| A37 | sec-Butyl | H | benzyl | 2.31 | 563/565/567 | B |
| A38 | (Tetrahydro-furan-2-yl)-methyl | H | benzyl | 2.2 | 591/593/595 | B |
| A39 | Benzyl | H | benzyl | 2.31 | 597/599/601 | B |

TABLE A-continued

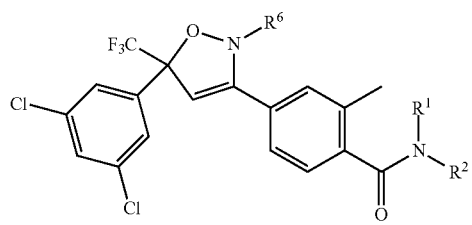

(Ib)

| Comp No. | R¹ | R² | R⁶ | RT (min) | MH⁺ | Method |
|---|---|---|---|---|---|---|
| A40 | 2-Fluoro-benzyl | H | benzyl | 2.32 | 615/617/619 | B |
| A41 | 1-Phenyl-ethyl | H | benzyl | 2.35 | 611/613/615 | B |
| A42 | 4-Methoxy-benzyl | H | benzyl | 2.29 | 627/629/631 | B |
| A43 | 1,1-Dioxo-thietan-3-yl | H | benzyl | 2.07 | 611/613/615 | B |
| A44 | (6-Chloro-pyridin-3-yl)-methyl | H | benzyl | 2.24 | 632/634/636 | B |
| A45 | 3-Fluoro-phenyl | H | benzyl | 2.39 | 601/603/605 | B |
| A46 | Pyridin-2-yl-methyl | H | benzyl | 2.07 | 598/600/602 | B |
| A47 | 2,5-Dimethyl-2H-pyrazol-3-yl | H | benzyl | 2.16 | 601/603/605 | B |
| A48 | 4-Methyl-thiazol-2-yl | H | benzyl | 2.34 | 604/606/608 | B |
| A49 | 3-Methyl-thietan-3-yl | H | benzyl | 2.33 | 593/595/597 | B |
| A50 | 1,1-Dimethyl-2-methylsulfanyl-ethyl | H | benzyl | 2.41 | 609/611/613 | B |
| A51 | 1-Oxo-thietan-3-yl | H | benzyl | 1.99 | 595/597/599 | B |
| A52 | Thietan-3-yl | H | benzyl | 2.24 | 579/581/583 | B |
| A53 | Bicyclo[2.2.1]hept-2-yl | H | benzyl | 2.43 | 601/603/605 | B |
| A54 | Cyclobutyl | H | benzyl | 2.28 | 561/563/565 | B |
| A55 | 2-Methane-sulfinyl-ethyl | H | benzyl | 1.94 | 597/599/601 | B |
| A56 | 2-Methyl-sulfanyl-ethyl | H | benzyl | 2.23 | 581/583/585 | B |
| A57 | Tetrahydro-thiophen-3-yl | H | benzyl | 2.26 | 594/596/598 | B |

TABLE B

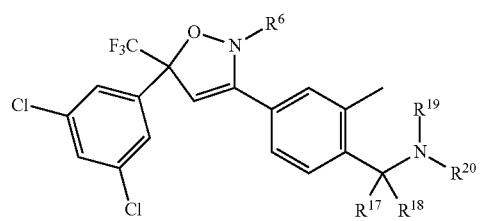

(Ic)

| Comp No. | R⁶ | R¹⁷ | R¹⁸ | R¹⁹ | R²⁰ | RT (min) | MH⁺ | Method |
|---|---|---|---|---|---|---|---|---|
| B1 | Methyl | H | H | Propionyl | H | 2.02 | 473/475/477 | B |
| B2 | Methyl | H | H | 2-Ethyl-butyryl | H | 2.23 | 515/517/519 | B |
| B3 | Methyl | H | H | 2-(1H-Tetrazol-5-yl)-acetyl | H | 1.84 | 527/529/531 | B |
| B4 | Methyl | H | H | Cyclohex-3-enecarbonyl | H | 2.21 | 525/527/529 | B |
| B5 | Methyl | H | H | 2-Bromo-butyryl | H | 2.21 | 565/567/569 | B |
| B6 | Methyl | H | H | 2-Methyl-cyclohexanecarbonyl | H | 2.36 | 541/543/545 | B |
| B7 | Methyl | H | H | 3-Phenyl-propionyl | H | 2.21 | 549/551/553 | B |
| B8 | Methyl | H | H | 2-(1H-Benzoimidazol-2-ylsulfanyl)-acetyl | H | 2.05 | 607/609/611 | B |

TABLE B-continued

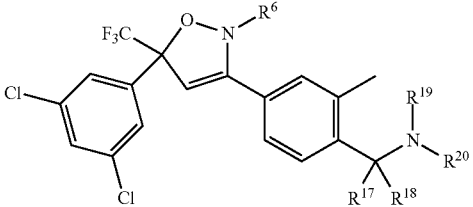

(Ic)

| Comp No. | $R^6$ | $R^{17}$ | $R^{18}$ | $R^{19}$ | $R^{20}$ | RT (min) | MH⁺ | Method |
|---|---|---|---|---|---|---|---|---|
| B9 | Methyl | H | H | Tetrahydro-furan-2-carbonyl | H | 2.08 | 515/517/519 | B |
| B10 | Methyl | H | H | (E)-3-Furan-2-yl-acryl | H | 2.15 | 537/539/541 | B |
| B11 | Methyl | H | H | 2-Benzyloxy-acetyl | H | 2.24 | 565/567/569 | B |
| B12 | Methyl | H | H | 2-Thiophen-2-yl-acetyl | H | 2.15 | 541/543/545 | B |
| B13 | Methyl | H | H | 2-Phenoxy-acetyl | H | 2.22 | 551/553/555 | B |
| B14 | Methyl | H | H | 2-Phenyl-acetyl | H | 2.17 | 535/537/539 | B |
| B15 | Methyl | H | H | 2-{3-Methyl-2-methylimino-4-oxo-thiazolidin-5-yl}-acetyl | H | 1.95 | 601/603/605 | B |
| B16 | Methyl | H | H | (E)-3-(2-Chloro-phenyl)-acryl | H | 2.3 | 581/583/585 | B |
| B17 | Methyl | H | H | (E)-3-(2-Fluoro-phenyl)-acryl | H | 2.24 | 565/567/569 | B |
| B18 | Methyl | H | H | 4-Oxo-4-phenyl-butyryl | H | 2.16 | 577/579/581 | B |
| B19 | Methyl | H | H | (E)-4-Oxo-4-p-tolyl-but-2-enoyl | H | 2.27 | 589/591/593 | B |
| B20 | Methyl | H | H | 2-(4-Chloro-phenoxy)-acetyl | H | 2.29 | 585/587/589 | B |
| B21 | Methyl | H | H | 2-(2-Phenyl-thiazol-4-yl)-acetyl | H | 2.3 | 618/620/622 | B |
| B22 | Methyl | H | H | 3-(1,3-Dioxo-1,3-dihydro-isoindol-2-yl)-propionyl | H | 2.09 | 618/620/622 | B |
| B23 | Methyl | H | H | 3-Methyl-1H-indene-2-carbonyl | H | 2.35 | 573/575/577 | B |
| B24 | Methyl | H | H | 2,3-Difluoro-benzoyl | H | 2.23 | 557/559/561 | B |
| B25 | Methyl | H | H | 3-Fluoro-4-hydroxy-benzoyl | H | 2.02 | 555/557/559 | B |
| B26 | Methyl | H | H | Benzo[1,2,5]thiadiazole-5-carbonyl | H | 2.22 | 579/581/583 | B |
| B27 | Methyl | H | H | 4-Methylsulfanyl-benzoyl | H | 2.25 | 567/569/571 | B |
| B28 | Methyl | H | H | 2,5-Dichloro-benzoyl | H | 2.3 | 589/591/593 | B |
| B29 | Methyl | H | H | 4-Methoxy-benzoyl | H | 2.16 | 551/553/555 | B |
| B30 | Methyl | H | H | 4-Pyrrol-1-yl-benzoyl | H | 2.28 | 586/588/590 | B |
| B31 | Methyl | H | H | 3,4-Dihydro-2H-benzo[b][1,4]dioxepine-7-carbonyl | H | 2.19 | 593/595/597 | B |
| B32 | Methyl | H | H | Biphenyl-4-carbonyl | H | 2.38 | 597/599/601 | B |
| B33 | Methyl | H | H | 2-Fluoro-3-trifluoromethyl-benzoyl | H | 2.32 | 607/609/611 | B |
| B34 | Methyl | H | H | 9H-Fluorene-4-carbonyl | H | 2.35 | 609/611/613 | B |
| B35 | Methyl | H | H | Benzo[b]thiophene-5-carbonyl | H | 2.27 | 577/579/581 | B |
| B36 | Methyl | H | H | 3-Methyl-pyridine-2-carbonyl | H | 2.29 | 536/538/540 | B |
| B37 | Methyl | H | H | Cinnoline-4-carbonyl | H | 2.07 | 573/575/577 | B |
| B38 | Methyl | H | H | 4-Methoxy-thiophene-3-carbonyl | H | 2.22 | 557/559/561 | B |
| B39 | Methyl | H | H | Thiophene-2-carbonyl | H | 2.15 | 527/529/531 | B |
| B40 | Methyl | H | H | 5-Methyl-3-phenyl-isoxazole-4-carbonyl | H | 2.26 | 602/604/606 | B |
| B41 | Methyl | H | H | 4-Oxo-4H-chromene-2-carbonyl | H | 2.16 | 589/591/593 | B |
| B42 | Methyl | H | H | 5-Pyridin-2-yl-thiophene-2-carbonyl | H | 2.21 | 604/606/608 | B |
| B43 | Methyl | H | H | 5-Methyl-1-phenyl-1H-pyrazole-4-carbonyl | H | 2.22 | 601/603/605 | B |

Biological Examples

Spodoptera littoralis (Systemic) (Egyptian Cotton Leaf Worm)

Test compounds were applied by pipette into 24 well plates and mixed with agar. Salad seeds were placed on the agar and the multi well plate is closed by another plate which contains also agar. After 7 days the roots have absorbed the compound and the salad has grown into the lid plate. The salad leafs were now cut off into the lid plate. Spodoptera eggs were pipette through a plastic stencil on a humid gel blotting paper and the plate closed with it. The samples are checked for mortality, repellent effect, feeding behavior, and growth regulation 5 days after infestation. Application rate: 12.5 ppm The following compound gave at least 80% control of Spodoptera littoralis: A5, A17, A21, A38, A53.

Spodoptera littoralis (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of Spodoptera littoralis: A4, A6, A7, A9, A10, A11, A12, A13, A14, A15, A16, A17, A19, A20, A21, A22, A24, A26, A31, A32, A35, A36, A42, A43, A46, A51, A52, A54, A55, A56, A57, B1, B5, B24, B36, C1.

Heliothis virescens (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of Heliothis virescens: A12, A13, A14, A16, A17, A18, A21, A22, A26, A27, A28, A31, A35, A39, A42, A43, A44, A45, A46, A48, A51, A52, A56, A57, BI, B14, B15, B24, B27, B29, B31, B37.

Plutella xylostella (Diamond Back Moth):

24-well microtiter plate (MTP) with artificial diet was treated with test solutions at an application rate of 200 ppm (concentration in well 18 ppm) by pipetting. After drying, the MTPs were infested with L2 larvae (7-12 per well). After an incubation period of 6 days, samples were checked for larval mortality and growth regulation.

The following compound gave at least 80% control of Plutella xylostella: A1, A2, A3, A4, A5, A6, A7, A9, A10, A11, A12, A13, A14, A15, A16, A17, A18, A19, A21, A22, A23, A24, A25, A26, A27, A28, A31, A32, A33, A34, A35, A38, A39, A40, A42, A43, A44, A46, A47, A51, A52, A54, A55, A56, A57, B1, B24, B37, C1.

Diabrotica balteata (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of Diabrotica balteata: A2, A3, A10, A12, A13, A14, A18, A21, A22, A23, A26, A28, A32, A35, A43, A51, A52, A57, C1.

Myzus persicae (Green Peach Aphid)

(mixed population, feeding/residual contact activity, preventive)

Sunflower leaf discs are placed on agar in a 24-well microtiter plate and sprayed with test solutions at an application rate of 200 ppm. After drying, the leaf discs are infested with an aphid population of mixed ages. After an incubation period of 6 days, samples are checked for mortality and special effects (e.g. phytotoxicity).

The following compounds gave at least 80% control of Myzus persicae: A18, C1.

Myzus persicae (Sachet) (Green Peach Aphid) Mixed Population

Test compounds were applied by pipette into 24 well plates and mixed with Sucrose solution. The plates were closed with a stretched Parafilm. A plastic stencil with 24 holes is placed onto the plate and infested pea seedlings were placed directly on the Parafilm. The infested plate is closed with a gel blotting paper and another plastic stencil and then turned upside down. 5 days after infestation the samples were checked on mortality. Application rate: 12.5 ppm. The following compounds gave at least 80% control of Myzus persicae: A5, A13, A16, A21, A22, A28, A52, B21.

Thrips tabaci (Onion Thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of Thrips tabaci: A1, A2, A4, A6, A7, A8, A9, A10, A11, A13, A14, A15, A16, A19, A20, A21, A22, A23, A24, A26, A27, A28, A35, A39, A43, A46, A52, A54, A55, A57, B1, C1.

Tetranychus urticae (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of Tetranychus urticae: A2, A4, A9, A10, A13, A14, A16, A19, A20, A21, A22, A26, A27, A28, A34, A35, A42, A43, A51, A54, A55, B12, B29, B38, C1.

The invention claimed is:

1. A compound of formula Int-II

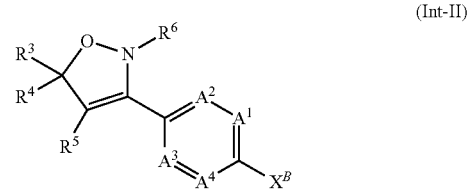

(Int-II)

wherein $X^B$ is a leaving group;

$A^1, A^2, A^3$ and $A^4$ are independently of each other C—H, C—$R^7$, or nitrogen;

$R^3$ is $C_1$-$C_8$haloalkyl;

$R^4$ is aryl or aryl substituted by one to five $R^{11}$, heteroaryl or heteroaryl substituted by one to five $R^{11}$;

$R^5$ is hydrogen;

$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkyleneor heterocyclyl-$C_1$-$C_4$alkylene- wherein the heterocyclyl moiety is substituted by one to five $R^{14}$, aryl or aryl substituted by one to five $R^{14}$, heterocyclyl or heterocyclyl substituted by one to five $R^{14}$, $C_1$-$C_4$alkoxycarbonyl-, $C_1$-$C_4$alkenyloxycarbonyl-, $C_1$-$C_4$alkynyloxycarbonyl-, or benzyloxycarbonyl- or benzyloxycarbonyl- in which the benzyl group is optionally substituted by one to five $R^{16}$;

each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^8$ is independently halogen, cyano, nitro, hydroxy, amino, $C_1$-$C_8$alkylamino, $(C_1$-$C_8$alkyl$)_2$amino, $C_1$-$C_8$alkylcarbonylamino, $C_1$-$C_8$haloalkylcarbonylamino, $C_1$-$C_8$alkoxy-, $C_1$-$C_8$haloalkoxy-, aryloxy or aryloxy substituted by one to five $R^{15}$, aryloxy-$C_1$-$C_4$alkylene or aryloxy-$C_1$-$C_4$alkylene wherein the aryl moiety is substituted by one to five $R^{15}$, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, or aryl-$C_1$-$C_4$alkylthio- or aryl-$C_1$-$C_4$alkylthio- wherein the aryl moiety is substituted by one to five $R^{15}$;

each $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxy-carbonyl-, aryl or aryl substituted by one to five $R^{15}$, or heterocyclyl or heterocyclyl substituted by one to five $R^{15}$;

each $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^{13}$ is independently halogen or $C_1$-$C_8$alkyl;

each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-; and each $R^{16}$ is independently halogen, cyano, formyl, $C_1$-$C_4$alkyl, $C_1$-$C_4$haloalkyl, $C_1$-$C_4$alkoxy, $C_1$-$C_4$haloalkoxy, $C_3$-$C_6$cycloalkyl;

or a salt or N-oxide thereof.

* * * * *